United States Patent
Henry et al.

(10) Patent No.: US 7,007,541 B2
(45) Date of Patent: *Mar. 7, 2006

(54) MULTI-PARAMETER MONITORING SYSTEM

(75) Inventors: Kent D. Henry, Laramie, WY (US);
Neal W. Syverson, Laramie, WY (US);
Ronny D. Harris, Laramie, WY (US);
Zachary A. Gray, Sheridan, WY (US);
Mark A. Watson, Laramie, WY (US);
Stanley B. Smith, Colorado Springs, CO (US)

(73) Assignee: In-Situ, Inc., Fort Collins, CO (US)

( * ) Notice: Subject to any disclaimer, the term of this patent is extended or adjusted under 35 U.S.C. 154(b) by 6 days.

This patent is subject to a terminal disclaimer.

(21) Appl. No.: 10/072,203

(22) Filed: Feb. 6, 2002

(65) Prior Publication Data

US 2003/0145646 A1    Aug. 7, 2003

(51) Int. Cl.
*G01N 33/00* (2006.01)
(52) U.S. Cl. ..................... 73/19.1; 73/61.41
(58) Field of Classification Search ............ 73/19.01, 73/152.02, 152.18, 152.51, 152.52, 866.5, 73/61.41
See application file for complete search history.

(56) References Cited

U.S. PATENT DOCUMENTS

| | | |
|---|---|---|
| 3,518,530 A | 6/1970 | Wilson |
| 4,620,189 A | 10/1986 | Farque ................. 340/856 |
| 4,624,309 A | 11/1986 | Schnatzmeyer .......... 166/66 |
| 4,662,210 A | 5/1987 | D'Aoust .................. 73/19 |
| 4,753,105 A | 6/1988 | Juanarena et al. .......... 73/4 |
| 5,099,920 A | 3/1992 | Warburton et al. ........ 166/250 |
| 5,166,910 A | 11/1992 | Batzle et al. ............ 367/191 |
| 5,259,452 A | 11/1993 | Wittrisch .............. 166/250 |
| 5,318,459 A | 6/1994 | Shields .................. 439/527 |
| 5,515,236 A | 5/1996 | Nolan et al. ............ 361/652 |
| 5,526,287 A | 6/1996 | French ................... 364/550 |
| 5,784,004 A | 7/1998 | Esfahani et al. ........ 340/854.6 |
| 5,820,416 A | 10/1998 | Carmichael ............ 439/668 |
| 5,821,400 A | 10/1998 | Sweeney, Jr. ........... 73/19.05 |
| 5,821,405 A * | 10/1998 | Dickey et al. ........... 73/53.01 |
| 5,957,200 A | 9/1999 | Majek et al. .......... 166/250.15 |
| 5,995,020 A * | 11/1999 | Owens et al. .......... 340/854.9 |
| 6,061,000 A | 5/2000 | Edwards .............. 340/854.6 |
| 6,165,005 A * | 12/2000 | Mills et al. ............. 439/489 |
| 6,305,944 B1 * | 10/2001 | Henry et al. ............ 439/22 |
| 6,356,205 B1 * | 3/2002 | Salvo et al. ........... 340/853.3 |
| 2003/0016128 A1 | 1/2003 | Lutz et al. ............. 340/517 |

OTHER PUBLICATIONS

Hydrolab Brochure "New Series 4a Water Quality Instruments From Hydrolab For Worry-Free Water Quality Data" dated Apr. 27, 1999.*

* cited by examiner

Primary Examiner—Charles Garber
(74) Attorney, Agent, or Firm—Robert G. Crouch; Marsh, Fischmann & Breyfogle LLP

(57) ABSTRACT

A plurality of multi-parameter monitoring tool assemblies are connectable over a communications network and are further in communication with a central controller. Each of the tool assemblies is configured to interconnect with one or more sensor head components which may be employable in the monitoring of water quality. According to the system described herein, the central controller may periodically communicate with one or more of the tool assemblies connected in the communications network and extract, process, and display information as to the configuration and operation of one or more tool assemblies.

8 Claims, 30 Drawing Sheets

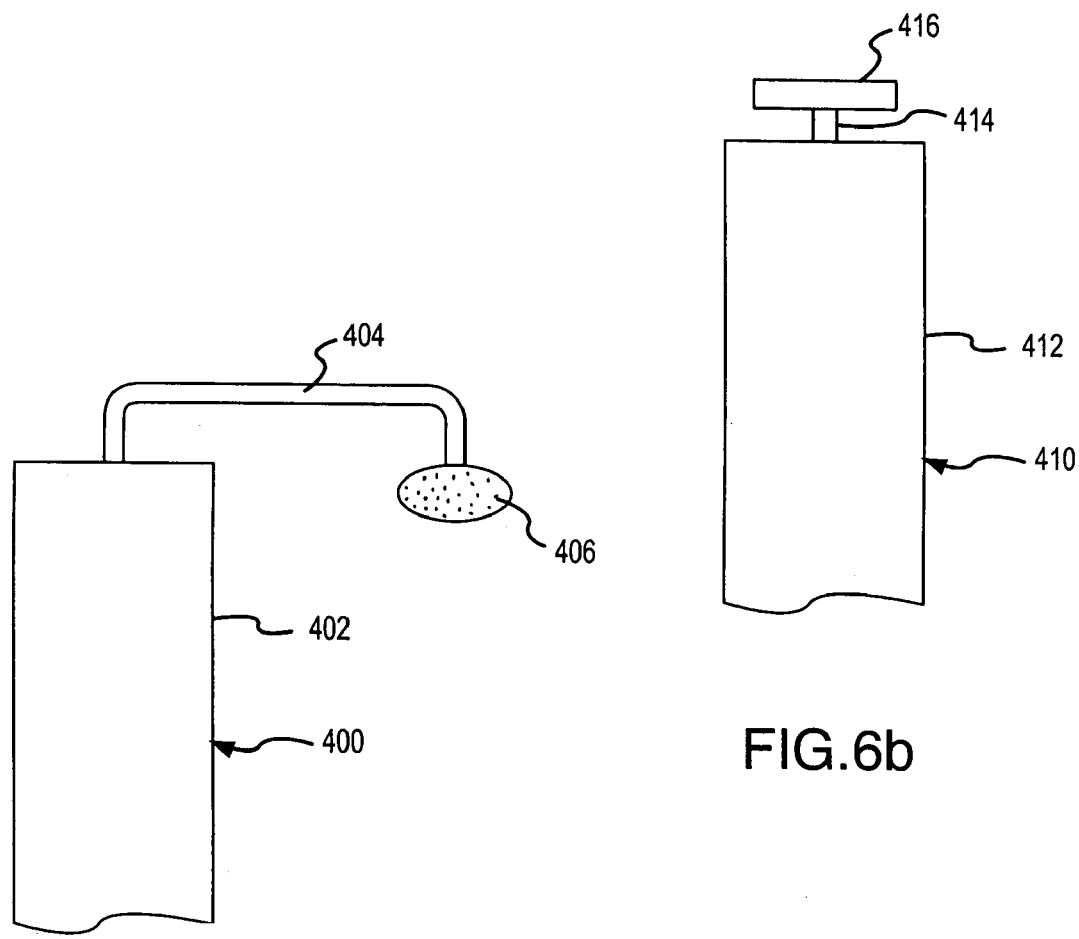
FIG.6a
FIG.6b
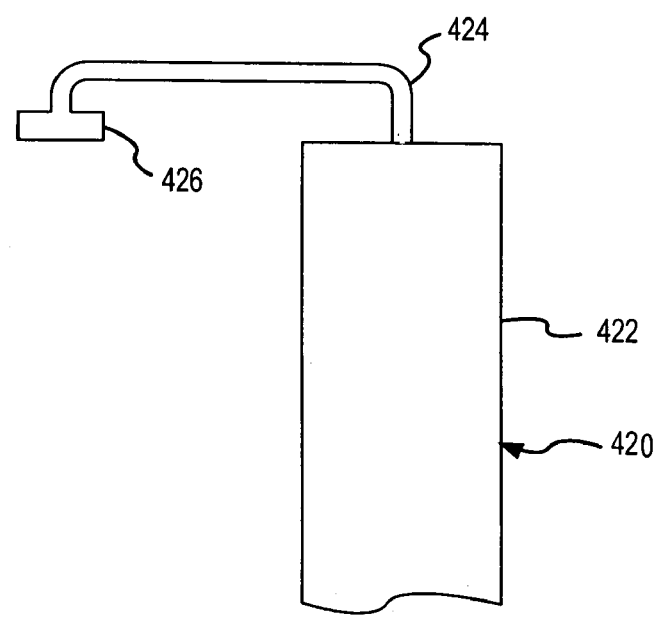
FIG.6C

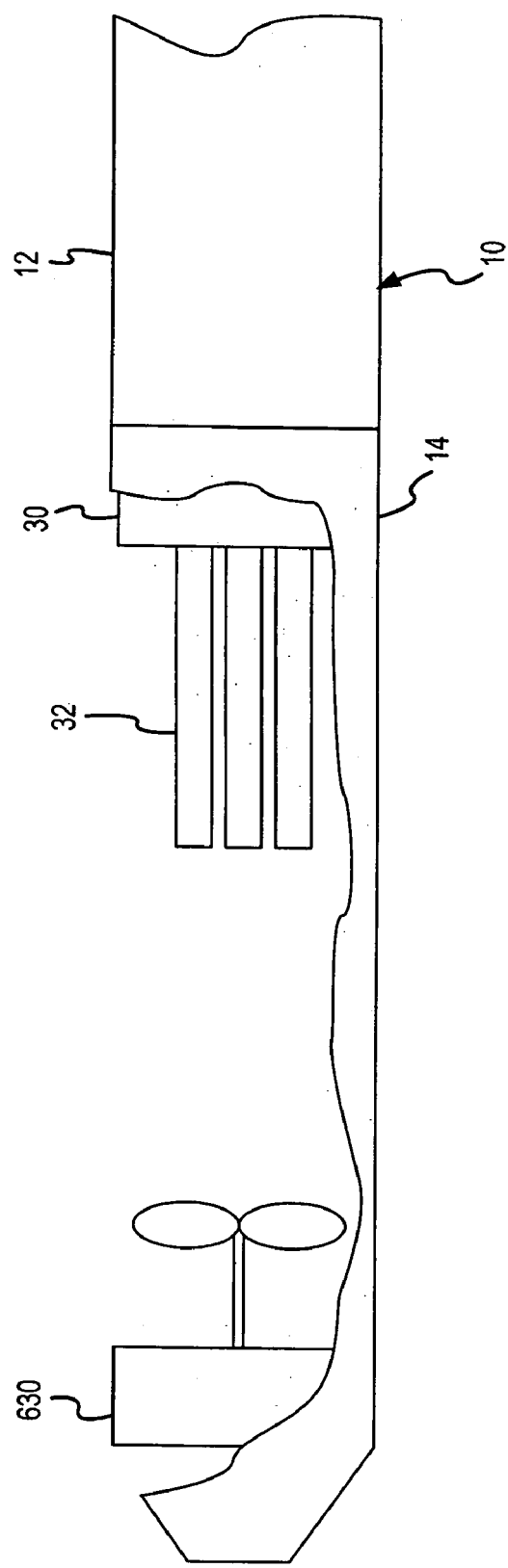

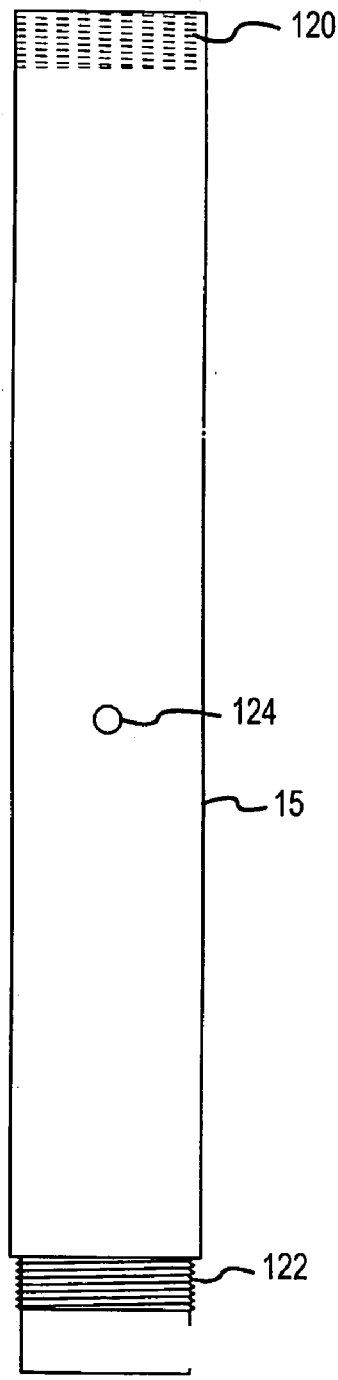
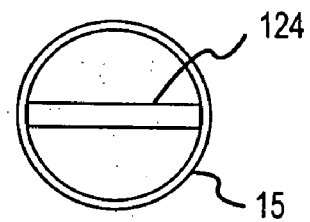
FIG.11b
FIG.11a

MULTI-PARAMETER MONITORING SYSTEM

FIELD OF THE INVENTION

The present invention relates to a tool assembly configured to monitor a plurality of conditions, and more particularly to a tool assembly configured to measure and store data for several water quality parameters, wherein the tool assembly is configured to receive and communicate with a number of interchangeable sensors.

BACKGROUND OF THE INVENTION

An ever increasing emphasis is being placed on systematic monitoring of environmental conditions in relation to ground and surface water resources. Examples of some situations where monitoring of conditions of a water resource may be desired include environmental monitoring of aquifers at an industrial site to detect possible contamination of the aquifer, monitoring the flow of storm water runoff and storm runoff drainage patterns to determine the affects on surface water resources, monitoring the flow or other conditions of water in a watershed from which a municipal water supply is obtained, monitoring lake, stream or reservoir levels, and monitoring ocean tidal movements.

These applications often involve taking data over an extended time and often over large geographic areas. For many applications, data is collected inside of wells or other holes in the ground. A common technique is to drill, or otherwise excavate, a number of monitoring wells and insert down-hole monitoring tools into the wells to monitor some condition of the water in the wells. One desirable feature of such a tool assembly is the capability to monitor one or more conditions at the site where the tool assembly has been located. In addition to such parameters as water level, temperature, and turbidity, it is also desirable to measure other parameters such water quality (i.e., the amount of contaminants in the water) which can be measured through the use of a conductivity sensor or other ion selective electrodes (ISE) sensors specially configured to detect the presence of one or more specific contaminants.

A significant issue with regards to the employment of tool assemblies for monitoring water quality conditions is the relatively high cost of each unit. One reason for the high cost is that they use expensive components and designs that frequently require a significant amount of expensive machining and assembly. The tools assemblies often require the complex assembly of many components and significant manufacturing expenses are often required to provide structures for coupling the components and for electrically interconnecting the components. Furthermore, assembly and disassembly of components of the down-hole tools frequently require the use of wrenches or other tools, and sometimes special tools. This complicates use of the down-hole monitoring tools, and providing features on the down-hole tools to accommodate tools required for assembly and disassembly often requires machining, which significantly adds to manufacturing costs. Furthermore, electrical interconnections between components typically require special keying of the components, or of the electrical connectors between the components which result in difficulty of use and a possibility for tool damage or malfunction due to misalignment.

In addition to the high cost of monitoring wells and down-hold monitoring tools, a significant amount of ongoing labor is typically required to maintain the tools and to obtain and use data collected by the tools. For example, it is frequently necessary to have someone visit the monitoring wells at periodic intervals to make sure that the tools are still working and to obtain data collected by the tools. Data must then be analyzed for use. The frequency between visits to a well may be a function of a number of variables, such as the reliability of the tools, the frequency with which batteries need to be replaced, and the capacity of the tools to collect and either store or provide access to the data. Moreover, many down-hole tools are difficult to service and must be returned to manufacturers and distributors for even relatively simple service tasks such as changing batteries in the tool. There is a significant need for tools that are simple to manufacture and assemble, require less attention, and are easier to service.

SUMMARY OF THE INVENTION

Described herein is a multi-parameter monitoring system which includes a plurality of multi-parameter monitoring tools connectable to a communications network, where each of the monitoring tools is configured to electrically interconnect with a plurality of interchangeable sensor head components. A central controller also connectable to the communications network, is configured to communicate with each of multi-parameter monitoring tools so as to extract operational information from the tool assembly which relates to the configuration of the sensor head components interconnected to the sensor head as well their operations.

The central controller is further configured to detect each of the multi-parameter tool assembly connected to the communications network, selectively access each of the tool assemblies and communicate so as to access, amend, and/or extract information stored in the tool assembly, relating to each of the interchangeable sensor head components interconnected with the access tool assembly. This selective accessing may be performed by placement of a unique address header in a message which is transmitted over in the communications network and identified by the addressed tool assembly.

The operational information extracted from a particular tool assembly may comprise identification information for the components interconnected in that tool assembly. According to the system described herein, the sensor head components may comprise sensors and/or accessories. In the configuration of the invention where the tool assembly is configured to monitor water quality in location such as ground water, surface water and flow cells, the interchangeable sensors may be configured for monitoring a number of parameter which includes: conductivity, dissolved oxygen, pressure and/or turbidity, oxidation reduction potential (ORP), chloride, nitrate, chlorophyll, ammonium, and temperature. In the configuration of the multi-parameter monitoring tool assembly where the sensor head component is a sensor, the operational information may include calibration data. In the configuration of the multi-parameter monitoring tool assembly where the sensor head component comprises an accessory, this accessory may be a stirring, wiper, and/or shutter device.

The communications network over which central controller communicates with the multi-parameter monitoring tool assemblies may comprise at least one of: the Internet, the public switch telephone network (PSTN), a wireless telephone, as well as radio waves. The multi-parameter monitoring tool assemblies may be located at a remote site wherein communications with a central controller are facilitated through use of a modem/controller device. This modem/controller device may be configure to emulate at least one other system such that communications may be established with devices other than the central controller.

The central controller may comprise any number of different devices which include: a personal computer, a palm top computer, a well top device, as well as another tool assembly. The central controller may be further configured so as to visually present information related to each of the multi-parameter tool assemblies in communications with the central controller over the communication network. The visual information may be presented on a screen display device which also provides for manual entry of information related to the operations of the multi-parameter tool assembly. As part of the central controller operations, the central controller is configured to detect when at least one tool assembly is connected to the network, detect the sensor head components interconnected with the tool assembly and present a first screen display which provides detailed configuration information for the particular tool assembly including data for each of the individual sensor head components connected thereto. Further, the sentral controller may present a second screen display which provides for manual entry of parameter information for each of the sensors included in the sensor head components. A third screen display may be presented for manual entry of testing information for each of the sensors, as well as extracting and compiling test information gather by the tool assembly during the monitoring process.

Additional functions performed by the central controller may include the upgrading and/or replacing of firmware resident in a particular multi-parameter monitoring tool assembly.

With regards to the use of sensors interconnected with a multi-parameter monitoring tool assembly, various testing procedures may be employed. One procedure in particular includes the monitoring of dissolved oxygen in a volume of water. The procedure may include first positioning the dissolved oxygen sensor in the liquid to be monitored. As was disclosed above, liquid may comprise ground water, surface water, or water within a flow cell. In order to begin the test, an electrical pulse of a predetermined magnitude is initiated across the electrodes in the dissolved oxygen sensor. At a second period of time after the initiation of the pulse, a measurement of the current magnitude across the electrodes is taken. Once this measurement is taken, a correction value related to the second period of time may be retrieved from memory and added to the measure value. This total comprises a final dissolved oxygen measurement which, depending on the configuration of the system, may be digitized and stored in memory for future access.

In order to conserve energy in the system, the first period of time may be equal the second period of time. That is, once a measurement is taken, the pulse may be terminated. Additionally, the above described measurement process may be performed on a periodic basis where each period is significantly longer than the first period of time.

The invention described herein may be further configured such that each of the multi-parameter monitoring tools in the system are configured to include at least one unactivated circuit connectable between a microprocessor device in the tool assembly and a sensor head component which is employable for monitoring at least one parameter. According to the system described herein, the unactivated circuit is further configured to include a high impedance buffer device so as to reduce current magnitude through the unpowered circuit. This high impedance buffer device provides the benefit of reducing stray currents which may interfere with system operations.

In one configuration of the invention, the high impedance buffer device may include a micro powered operational amplifier. This operational amplifier may be connectable in a circuit with either an active or passive sensor. In the configuration where the operational amplifier is connectable to an active sensor, this circuit may further include a capacitive device connectable at the operational amplifier output which minimizes current drive to un-powered circuitry, and a resistive element connected between ground and the output of the operational amplifier which provides dc bias.

In the circuits where the operational amplifier is connected to a circuit with a passive sensor, a large magnitude resistive element may be connectable at the output of the operational amplifier. The resistive element minimizes current drive to unpowered circuitry.

BRIEF DESCRIPTION OF THE DRAWINGS

FIGS. 6a–c discloses three configurations of an accessory.

FIG. 11a-b discloses views of the inner housing.

DETAILED DESCRIPTION

The present invention comprises a multi-parameter tool assembly employable for monitoring conditions in any number of locations, including ground and/or surface water, as well as within a flow cell. These locations may include insertion into a well or other hole. Specifically included in the multi-parameter tool assembly is a sensor head specially configured to receive and interconnect with one or more sensor head components. The sensor head components may comprise such things as a sensor or an accessory. The sensors may each be employable for monitoring a particular parameter. Further included in the multi-parameter tool assembly is an electronic system configured to direct at least one operation of the tool assembly and preferably substantially all operations. The electronic system may include a processor and memory having stored instructions readable and executable so as to direct operation. When one or more sensors are mounted in the sensor head, the computing unit is configured to identify and communicate with each of the sensors so as to take and process measurements. The multi-parameter tool assembly is also configured for interconnection with a data line so as to communicate with other systems, such as a central controller over data network.

Figure 1A:
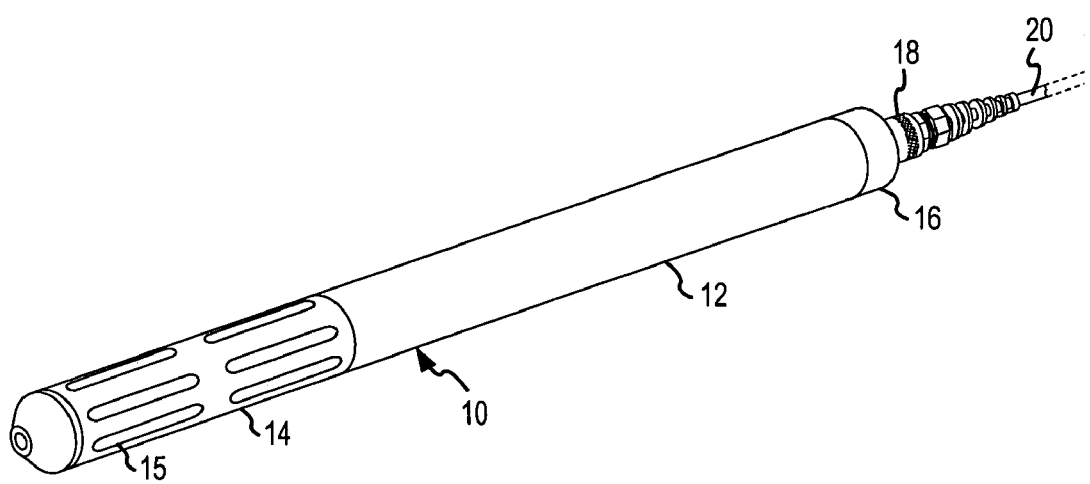
FIG. 1a discloses a geometric view of the multi-parameter monitoring tool and FIG. 1b discloses an exploded view of same.
Figure 1B:
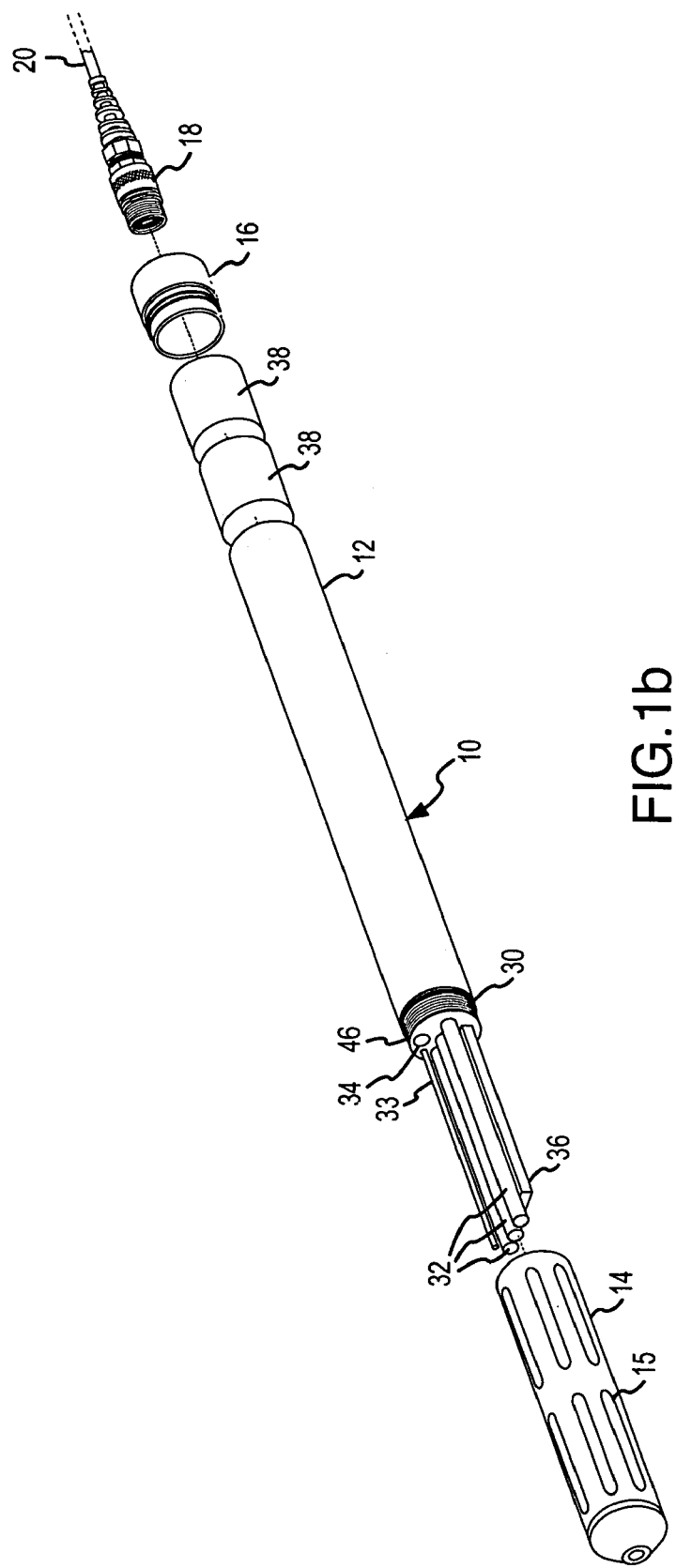

Disclosed in FIGS. 1a and 1b are assembled and exploded views, respectively, of the multi-parameter monitoring tool 10. The monitoring tool comprises a body portion 12 which is substantially cylindrical in shape, and enclosed within are the computing and power source components of the monitoring tool. Extending from the body portion 12 is an enclosure device 14, which in this view is a restrictor, which is also substantially cylindrical in shape. Formed in the restrictor are holes 15 which provide for the flow through of the liquid which is to be monitored. Although a restrictor 14 is shown in the embodiment of the invention shown in FIG. 1a, other enclosure devices, which will be described in greater detail below, are attachable to the tool assembly.

At the opposite end of the monitoring tool 10 is removable backshell 16, which as will be described in greater detail below, provides for easy access to batteries which are employed as a power source and are contained within the body portion 12. In connection with the battery removal backshell 16 is data quick-connect 18, which provides connections from one or more remote locations to the tool assembly, and is configured such that it is removable without the necessity of disconnecting the internal power source.

Disclosed in FIG. 1b is an exploded view of the multi-parameter monitoring tool and shown in particular is sensor head 30, which is connectable with body 12 in a manner which will be describe in greater detailed below. Included on the sensor head portion is a male threaded portion 46, which is configured to engage female threads on enclosure device 14. Configured in the sensor block 30 are one or more ports 34. As will be discussed in greater detail below, the ports 34 are specially configured to receive and engage an interchangeable sensor head component 32. In one configuration of the invention, the interchangeable sensor head components 32 are substantially cylindrical in shape, however, both the ports 34 and the interchangeable sensor head components may be configured in other shapes depending on the particular parameter being monitored or function to be performed. As an example, pressure sensor 36 is substantially rectangular in shape but is still received by a specially configured sensor port in sensor head 30. Although the configuration as shown only includes five sensor ports for receiving interchangeable sensor head components, it is conceivable that this number may be increased or decreased depending on the particular environment within which the monitoring tool is operating and the available space in the tool.

As was mentioned above, the body portion 12 is configured to receive one or more replaceable batteries 38. In the preferred embodiment of the invention, the batteries are standard D-size cells, however, depending on the space available and the electronic configuration, other types of power cells may be employable. The replaceable batteries 38 are locatable within the housing 12 and accessible through removable backshell 16. Incorporated into removable backshell 16 is a female threaded portion which is specially configured to engage a male threaded portion (not shown) of the housing 12. Also included in the removable backshell 16 is a female threaded portion configured to receive and engage with a male threaded portion configured on a data quick-connect 18. Certain electrical connections, to be disclosed below, are included in both the data quick-connect 18 and removable backshell 16 in order to provide for data connections.

Figure 2C:
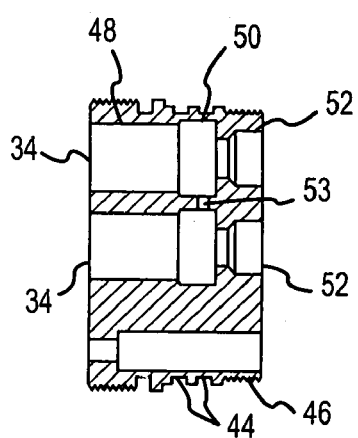
FIGS. 2a–c discloses various views of the multi-parameter sensor head.
Figure 2B:
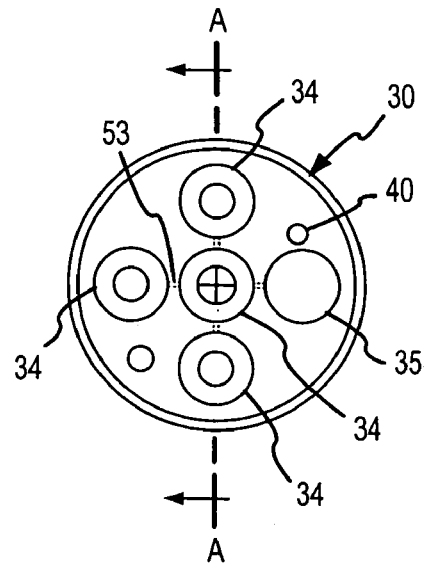
Figure 2A:
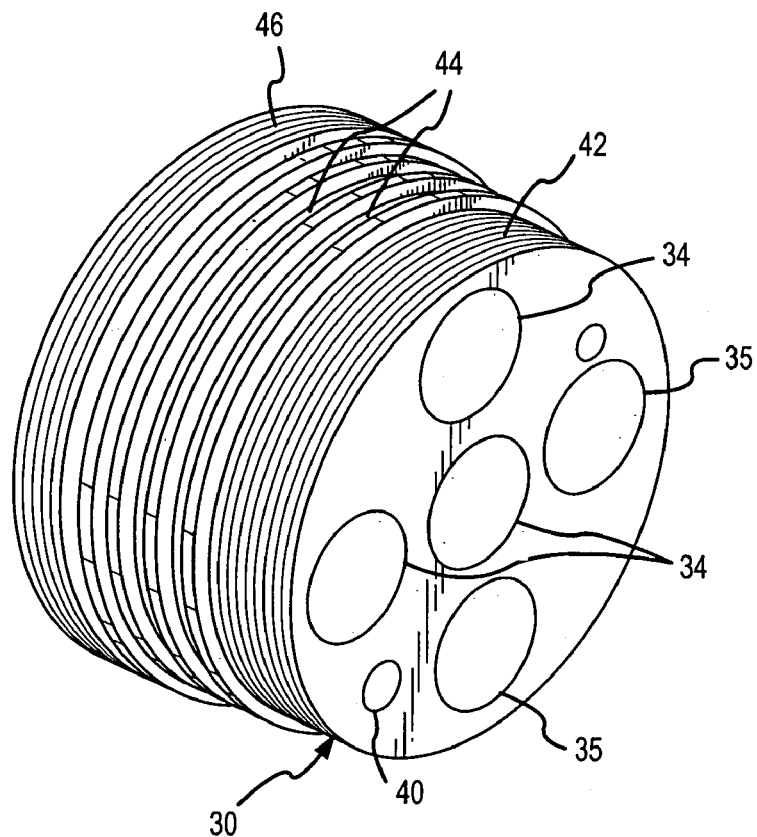

Disclosed in FIGS. 2a–c are detailed views of sensor head 30. As was discussed above, the sensor head 30 includes a number of sensor ports for receiving one or more interchangeable sensor head components. Specifically, the sensor head 30 may be configured to include a number different ports, such as port 34 which provide for engaging the interchangeable sensor head components, wherein other ports, such as ports 35 and 40 may provide for engaging and interconnecting with components other than those which are interchangeable. The sensor head 30 includes a number of features employable in the assembly of the monitoring tool. Specifically, included therein is a threaded portion 42 which is configured to rotateably engage the enclosure device 14. Also included are a number of grooves 44 which receive a radially compressible sealing device such as an O-ring, gasket, or similarly configured component. These sealing devices provide, at least partially, for the engagement of the sensor block 30 with the body portion 12. The threaded portion 46 of sensor block 30 also provides for the engagement of the sensor head 30 with the body portion 12.

Shown in FIG. 2c is a cross-sectional view of the sensor head 30. Shown in particular is the configuration of the sensor ports 34 port which receives and engage the interchangeable sensors. Each sensor port 34 comprises a receiving hole 48 which is of a first constant diameter, where the receiving hole extends within the sensor head 30 to a predetermined depth. At the predetermined depth, the hole diameter expands to a second constant diameter 50 for a further depth in the sensor head. At the bottom of hole 48 is receptacle 52 which is specially configured to receive and engage a connector which is further configured to electrically connect with the interchangeable sensors when inserted in sensor port 34.

Sensor head 30 also includes an atmospheric pathway 53 which interconnects the bottom portion of each of the sensor ports. In the preferred configuration, each of the sensor ports 34 located around the outer perimeter of the sensor head 30 include an atmospheric pathway which provides an interconnection to the sensor port 34 in the center position of the sensor head. This atmospheric pathway between each sensor port reduces back pressure which may be created upon insertion of an interchangeable sensor head component in sensor head 30.

Figure 3B:
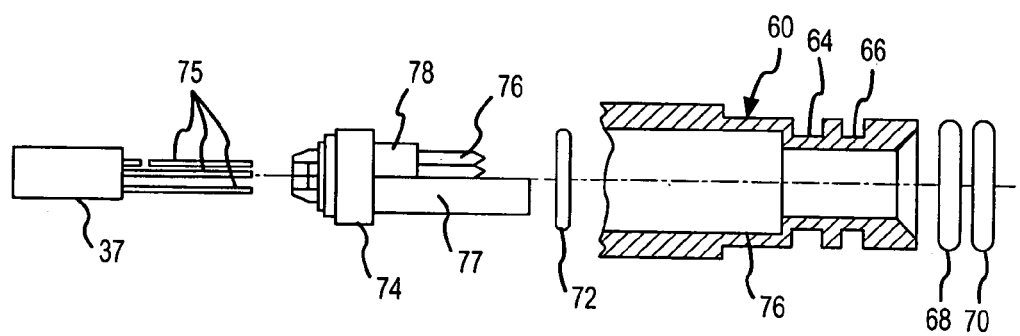
FIG. 3a discloses a geometric view of an interchangeable sensor head component and FIG. 3b discloses an exploded view of same.
Figure 3A:
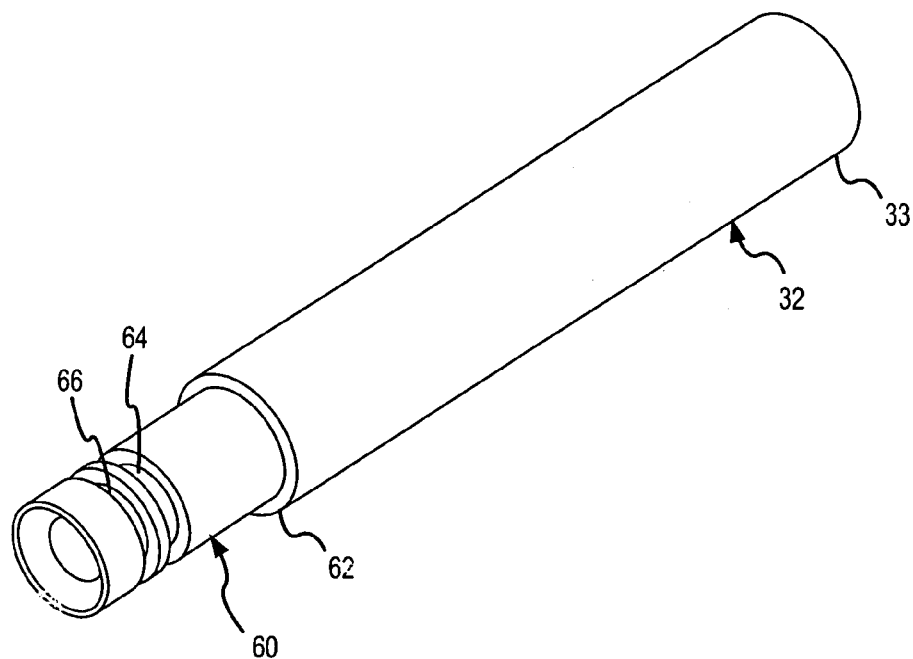

Disclosed in FIGS. 3a and 3b are various views of the interchangeable sensor head component 32 which includes plug 60. As is shown in FIG. 3a, plug 60 is substantially cylindrical in shape and includes removal lip 62, which extends around the circumference of the plug, as well as grooves 64 and 66 within which a radially compressive sealing device may be positioned. The embodiment of the interchangeable sensor component shown in FIG. 3a is a sensor 33, which is substantially cylindrical in shape and is sized to be positioned in plug 60. The sensor 33 may comprise any number of different types of water quality sensors which are employable in monitoring any number of parameters. These parameters may include conductivity, dissolved oxygen, oxidation reduction potential (ORP), as well as detection of trace elements such as nitrates, chlorides, and ammonium. Portions of the internal configuration and operation of these interchangeable sensors will be discussed in greater detail below. It should be noted that sensors such as those which are employed to measure pressure, turbidity, and temperature, may have a different configuration than a typical interchangeable sensor, and thus the sensor head 30 includes other ports to specially receive such a sensors.

Shown in FIG. 3b, is an exploded partial view of the sensor head component 32 including sensor plug 60. As is seen, the interchangeable sensor head component 32 includes a number of electrical leads 75 which are connectable to a number of electronic components including EEPROM 37. As will be discussed below, the EEPROM 37 is employable for storing and providing access to identification and other information about the sensor head component. The EEPROM 37 and electrical leads are positionable within plug 60. The electrical connector 74 may include a number of male electrical electrode 76 and a female electrodes 77 which provide for a plug-in engagement of the component with matching male and female electrodes within a port of the sensor head. Radially compressive sealing device 72 is positionable around a portion of the connector 74 and is insertable within cavity 76 so as to provide an environmental seal for the electrical connections.

As was mentioned above, the plug 60 includes grooves 64 and 66. These grooves are specially configured to receive radially compressive sealing devices such as the O-rings 68 and 70 shown in FIG. 3b. The purpose of the O-rings is to provide for a secure environmentally sealed engagement of the interchangeable sensor head device in the sensor head 30. According to the present invention, the use of threaded engagements for the interchangeable sensor head components has been avoided, as well as all of the necessary manufacturing and space considerations which go with threaded configurations.

In order to engage and disengage an interchangeable sensor head components in one of the ports 34 in the sensor head 30, the plug portion of the interchangeable sensor is initially aligned with a selected port 34 such that the male and female electrodes of both the sensor plug and port are aligned. Once this is complete, the cylindrical portion of the sensor plug 60 is inserted in the selected port 34 such that both O-rings, 68 and 70, of the plug 60 pass into the hole of the first constant diameter 48. As the plug 60 is pushed further into port 34, the male and female electrodes, 76 and 77 of the plug 60 will engage with those extending into the sensor head and the bottom portion of the plug 60, will contact the bottom of the receptacle. Upon full insertion, the O-ring 70 positionable in the O-ring groove 66, will pass into the hole of the second diameter 50 and expand to fill the gap providing an environmental seal and creating a force for resisting ejection or removal forces on the sensor along its longitudinal axis. When fully plugged in, the second O-ring 68 will remain in the hole of the first constant diameter 48 and also act as an environmental seal.

Upon insertion of the sensor plug 60 in port 34, the atmosphere pathway 53 allows gases which would otherwise be trapped in the sensor port to pass out of other ports which do not currently have a sensor plug inserted therein. The atmospheric pathways incorporated throughout the sensor head further provide that in the situation where the final interchangeable sensor is inserted when the other ports are filled, that the pressure built up caused by such insertion is shared by all of the interconnected sensor ports. The interchangeable sensor head components may be removed by applying an opposing linear force, using removal lip 62, of sufficient magnitude to compress the O-ring 70 into the first constant diameter hole 48, and applying the force until the interchangeable sensor is removed.

As was mentioned above, the sensor head components may comprise various devices such as interchangeable sensors or accessories. The interchangeable sensors typically are configured to monitor one or more parameters and the physical component for monitoring the parameter are enclosable within housing 33. The interchangeable sensors typically comprise one of two types. The first type of sensor employed in the monitoring tool is a passive sensor. Passive sensors do not require external power and typically only require an electrical circuit connectable across the sensing element. Different types of passive sensors include temperature sensors and chemical detection sensors employing ion selective electrodes (ISE).

A second type of interchangeable sensor is an active sensor which requires external power source in order to perform its monitoring functions. Typically, an active sensor will include at least two additional electrical leads to conduct power to the sensor electronics. Examples of active sensors employable in the monitoring tool are pressure, conductivity, dissolved oxygen, and turbidity sensors.

According to the invention described herein, each sensor (either passive or active) may be further configured to monitor multiple parameters. As such, each probe may be configured with multiple passive and/or active sensing elements. Electrical connections to the probe may be configured such that unique signals generated by the different sensing elements may be identified and read by the tool assembly electronics.

Figure 4A:
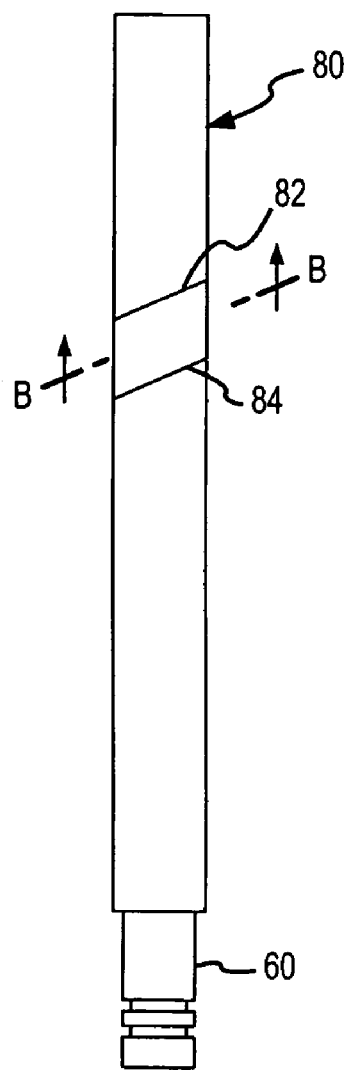
FIGS. 4a and b disclose various views of a first embodiment of the conductivity sensor.
Figure 4B:
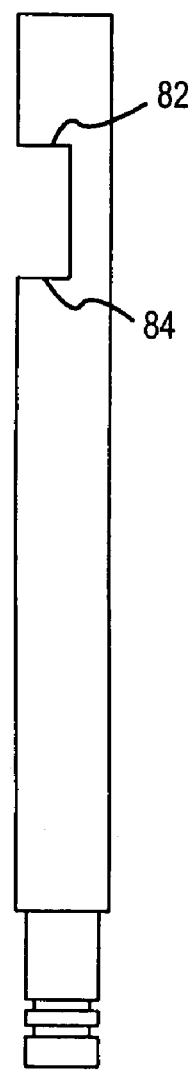

As was mentioned above, one type of interchangeable sensor which is employable with the multi-parameter monitoring tool is a conductivity sensor. Shown in FIGS. 4a and b is one configuration of a conductivity sensor 80 which is employable for monitoring the amount of contaminants or other foreign substances which may be contained in the water. In the configuration shown, the conductivity sensor 80 includes two slanted surfaces 82 and 84 incorporated into the cylindrical body. Electrodes employed in measuring conductively are positionable on the slanted surface. The use of the slanted surfaces provides the distinct advantage that as the multi-parameter monitoring tool assembly is placed in the liquid to be monitored, in typical vertical positioning, air bubbles will not form on one or more of the electrodes interfering with the taking of accurate readings.

Figure 5C:
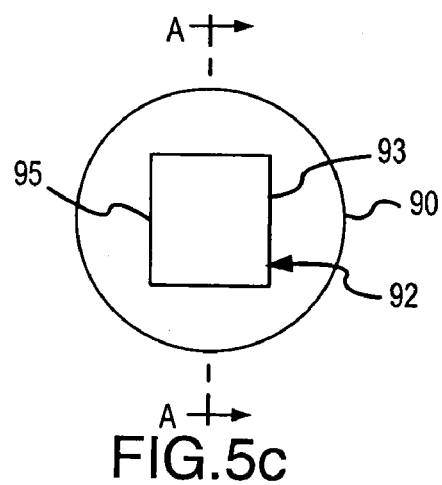
FIGS. 5a–c discloses various views of a second embodiment of the conductivity sensor.
Figure 5A:
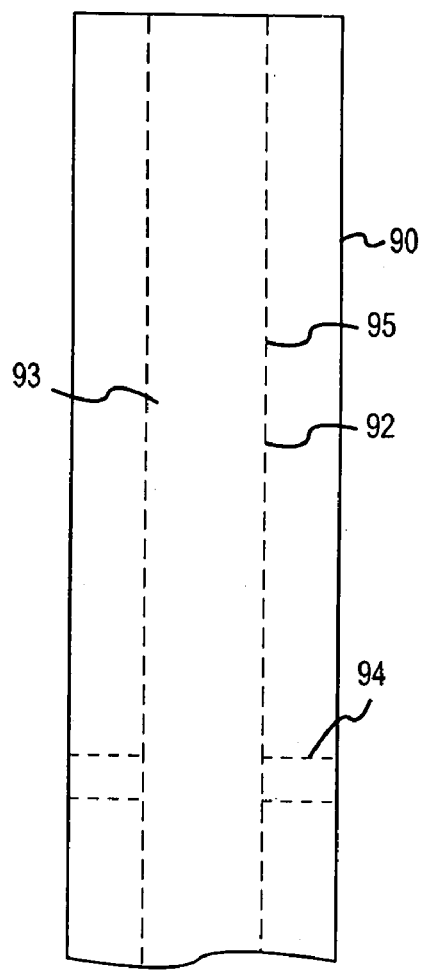
Figure 5B:
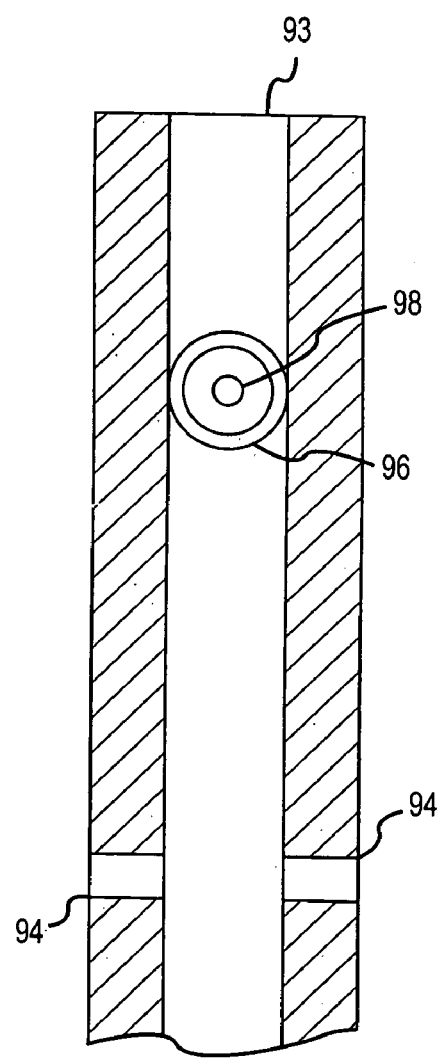

Another configuration of a conductivity probe is disclosed in FIGS. 5a–c. The probe 90 in this configuration includes an internal channel 92 with at least two opposing surfaces 93 and 95. Positionable on each of the opposing surfaces are the electrodes employed by the system in monitoring the conductivity of the water. Shown in FIG. 5b is a cross-sectional view of the probe, which shows in particular opposing surface 93 with electrodes 96 and 98 positioned thereon. Positioned opposite electrodes 96 and 98 on surface 95 is another set of electrodes (not shown). Also passing through the body of probe 90 are vent holes 94. These vent holes are employable such that when the conductivity probe is submerged in water (and positioned vertically) any air bubbles which may have been trapped in channel 92 will pass out hole 94 and will not interfere with any conductivity measurements.

As was mentioned above, sensor head components may also be configured as various types of accessories. These accessories may include one or more mechanical or electro mechanical components configured for performing a particular task. Accessories, as with the sensors, are installable in plug 60. The body portion which extends upwards from the plug portion would include the necessary electro-mechanical components for performing a designated task.

Disclosed in FIG. 6a-c are some possible configurations for accessories. Although the applicant shows only three possible configurations, any number of electrical or electro-mechanical devices may be employable as an accessory. Disclosed in FIG. 6a is an accessory which is employable with an interchangeable sensor that has an external window which may periodically require cleaning. One example is a turbidity sensor. The accessory 400 shown in FIG. 6a includes a mechanical arm 404 which extends from the body 402. On the end of the mechanical arm is a wiper device 406. When installed in the sensor head, the mechanical arm 404 provides for extending the wiper portion over to the window on the interchangeable sensor and moving in a fashion so as to clear any obstructions, such as algae or other substances, disposed on the window of the sensor. Once the cleaning portion is finished the wiper portion moves away and is locked in position until it is again activated.

Disclosed in FIG. 6b is an accessory 410 configured as a stirring device. Contained with the body portion 412 may be an electrical motor and extending from the motor outside the body may be a drive shaft 414 upon which stirring component 416 may be mounted. Upon activation, the electrical motor will spin the stirring component for a period time.

Disclosed in FIG. 6c is a shutter device which can be used either alone or in combination with the wiper device. Included in the shutter device is a mechanical arm 424 which extends from the body 422 of the sensor head component. Connected at the end of said arm is a shutter 426 which includes a portion which reflects light at a known wavelength. When the arm is activated, the shutter device can be positioned in front of the window of the sensor and since the visible portion reflects light at a known wave length it is employable to calibrate the sensing portion of the turbidity sensor. Once the calibration process is complete, the mechanical arm is employed to move the shutter away from the sensor and lock in place until a recalibration is requested. In one configuration of the accessory the wiper and shutter may be combinable in a single accessory.

Figure 7A:
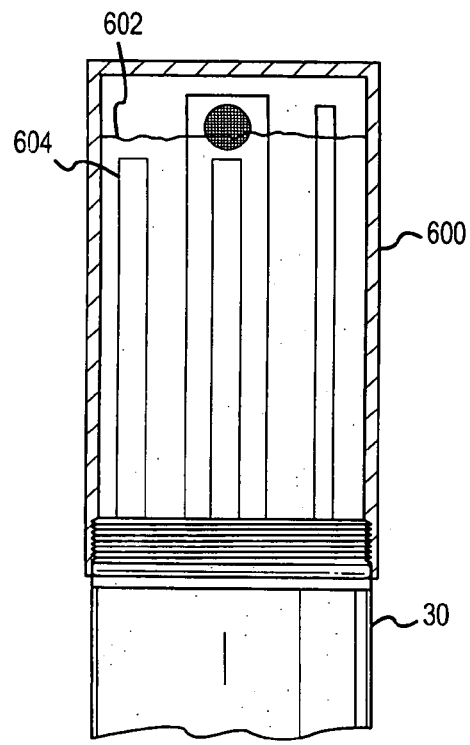
FIGS. 7a–b discloses two configurations of an enclosure device.

Referring again to FIG. 1b, and FIG. 2a, it was noted that the sensor head 30 includes a threaded portion 42 for engaging a number of different tool assembly component. In FIG. 1b, it was shown that the sensor head 30 may engage the restrictor device 14. The restrictor device 14 is ideal for exposing the water source to be monitored to the sensors, but still providing physical protection for these components. Two other components which are attachable to sensor head 30 are disclosed in FIG. 7a and b. Disclosed in FIG. 7a is a calibration cup 600 which is configured to threadably engage threads 42 of the sensor head so as to provide a environmental seal. The calibration cup is configured such that a calibrating solution 602 may be poured into the cup and then the cup attached to the sensor head such that each of the sensors may be exposed to the calibration solution. Once the calibration cup is attached to the tool assembly it may be reoriented in a different position so that one or more of the sensors 604 may be submerged and then exposed to atmosphere trapped within the calibration cup.

Figure 7B:
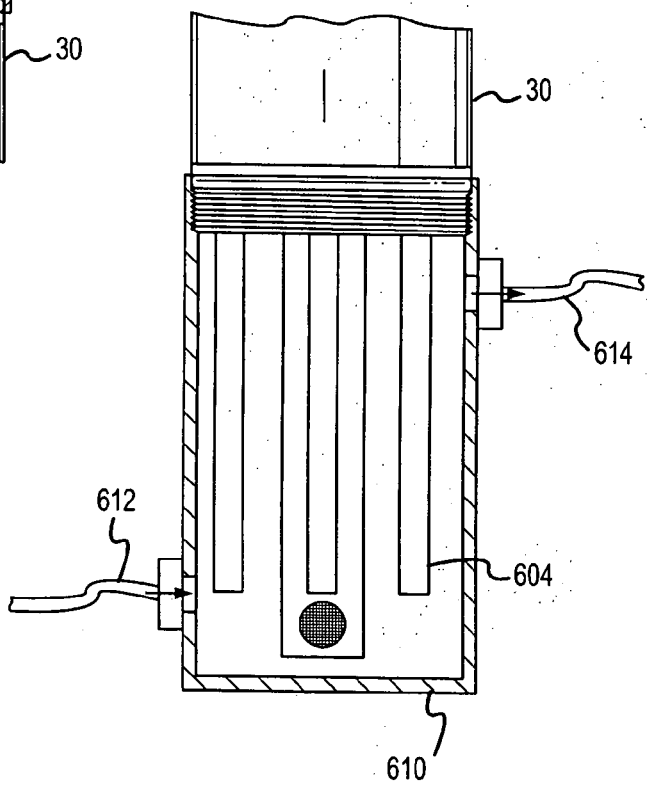
Figure 8A:
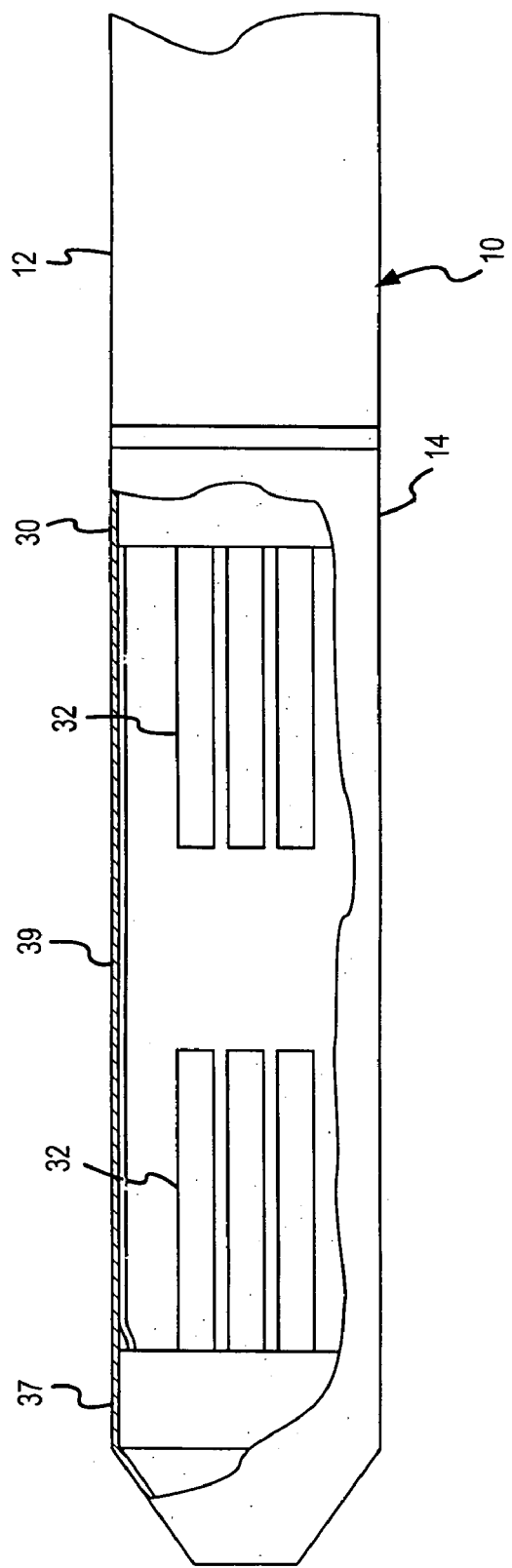
FIG. 8a discloses a breakaway view of the enclosure device including a second sensor head and FIG. 8b discloses a breakaway view of the enclosure device including stirring mechanism.

Disclosed in FIG. 7b is a configuration of the tool assembly wherein a flow cell 610 is attached to the sensor head 30. The purpose of a flow cell 610 is to provide a means to expose the sensors in a tool assembly to a remotely located liquid source. Included as part of the flow cell is an inlet line 612 and an outlet line 614. The inlet and outlet are connected to one or more remote reservoirs or sources of the liquid to be monitored. The size of the input and output lines are known so that the rate of fluid passing through the flow cell is calculable In yet another configuration of the invention, the tool assembly may be further configured to provide a greater amount of monitoring by employing a second sensor head. According to the configuration shown in FIG. 8a, a second sensor head 37 may be positioned within restrictor 14 or other enclosure device, opposite the first sensor head 30. As with sensor head 30, sensor head 37 includes a plurality of ports (not shown) which are substantially similar to those in sensor head 30 and are configured to receive and electrically engage one or more of the interchangeable sensor head components. A ribbon cable 39 may provide for the electrical interconnection between the sensor head and the electronics enclosed in housing 12.

Disclosed in FIG. 8b is yet another configuration of the tool assembly wherein a stirring device 630 is positionable proximate to the plurality to sensor head components positionable in the first sensor head. The stirring device 630 may be connectable to the restrictor or any other enclosure device described above. An electrical connection may or may not be established between the stirring device 630 and the electronics contained within the tool assembly. The stirring device may comprise an electric motor with a drive shaft and propeller device which moves the liquid in a desired fashion. In another configuration of the invention, the stirring device may comprise a magnetic stirrer wherein a spinning magnet provides for the desired movement of the liquid.

Figure 9:
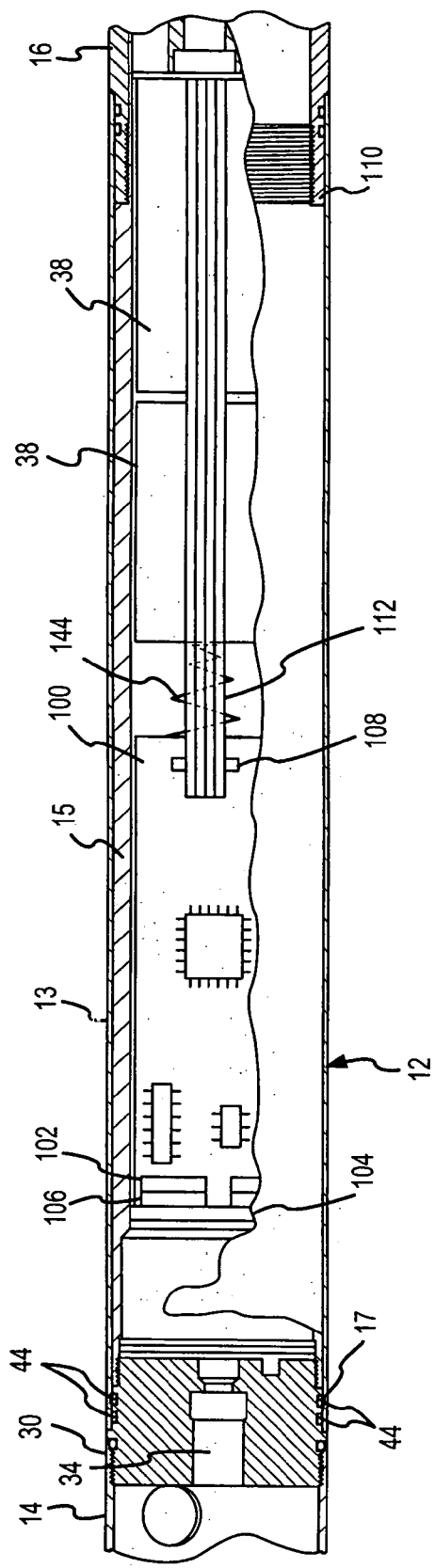
FIG. 9 discloses a breakaway side view of the multi-parameter monitoring tool.

Disclosed in FIG. 9 is a cutaway view of the multi-parameter monitoring tool 10, showing in particular the internal electrical components. Included therein are two circuit boards 100 and 104 which provide for the signal processing of the tool assembly. Circuit board 104 is mounted at the end of the sensor block 30 opposite the ports 34. The circuit board 104 is in electrical connection with a main circuit board 100 which in turn is connected via contact 108 to ribbon cable 112. This cable, in turn, extends to the far end of the assembly. Also shown are battery contact spring 144, as well as battery stop 113.

Figure 10:
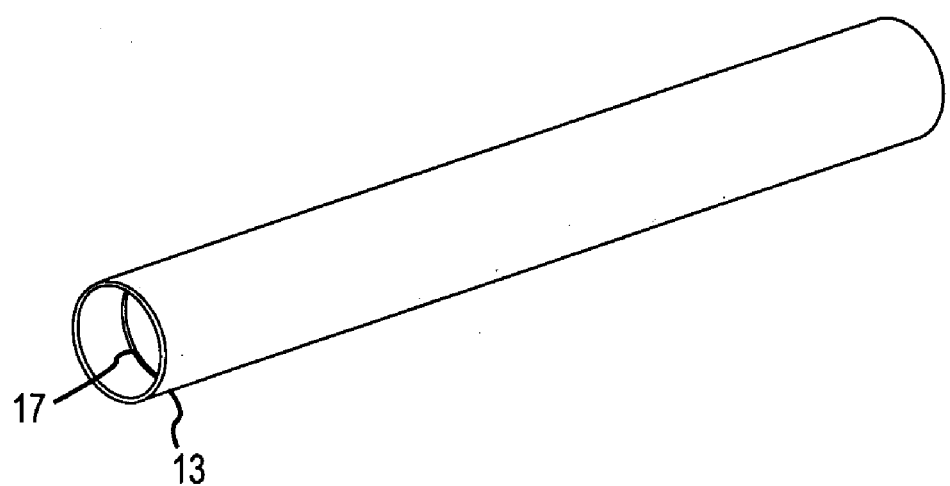
FIG. 10 discloses a perspective view of the outer housing.

The housing 12 may comprise any number of layers. In the configuration shown herein, an inner and outer housing are included. The outer housing 13, as shown in FIG. 10, may be manufactured of any number of different materials such as stainless steel or plastic. The outer housing 13 is configured as a cylinder without inner or outer engagement threads so that it would require a minimum amount of machining to manufacture. In order to engage with other components of the tool assembly, the inner diameter of the housing 13 is machined at a close tolerance. Also included a pre-determined distance from the opening at one end of the outer housing is an internal groove 17 machined at a designated depth.

With regards to assembly of the outer housing with the sensor head 30, it was previously mentioned that the sensor block 30 includes grooves 44. The portion of sensor block 30 where the grooves are formed has an outer diameter, which is marginally less than the inner diameter of the housing 13. Positionable within the grooves 44 may be any number of radially compressible sealing devices. These devices may include O-rings, gaskets, or an X-seal. For description purposes only, O-rings will be described as positionable in the grooves. During assembly of the tool, the bottom end of the sensor block 30, including O-rings, is placed within the outer housing 12 such that the O-rings are compressed against the interior surface of the housing 13. Upon full engagement, the outer housing will contact a stop portion of the sensor block 30. The compressed O-rings provide for an environmental seal as well as a mechanical force which resist disassembly of the components. In addition to, or as an alternate environmental seal, a flat compressive gasket may be positioned between the stop portion of the sensor head and the end of the outer housing 13.

Also employed in the assembly process between the outer-housing 13 and the sensor head 30 is the groove 17 machined into the interior surface of the outer housing 13. Referring again to FIG. 10, this groove is positioned at a pre-determine distance within the outer housing 13, such that upon assembly of the sensor head and outer housing, this groove partially engages one of the O-rings disposed around the sensor head. This partial engagement provides for a condition such that a desired resistive force is created which resist rotation of the outer housing relative to the sensor head 30. The additional resistive force provides for easier assembly and disassembly of components at the opposite end of the outer housing. The housing 13 also engages the battery removal backshell 16 in a substantially similar manner, although without the use of a machined groove. The configuration of the battery removal backshell 16 and its engagement with the outer housing will be described in greater detail below.

The second portion of the housing 12 is inner housing 15 which is positionable within the outer housing 13. The inner housing may be comprised of a plastic material, although one skilled in the art would realize that this component may be constructed of many different rigid materials. Disclosed in FIGS. 11a and b are side and front views, respectively, of the inner housing 15. Both ends of the inner housing 15 include threaded portions for engaging other components. Specifically, female threads 120 configured on the interior surface of the inner housing 15 are employable for engaging the male threads 46 on sensor block 30. The male threads 122 disposed on the outer surface of the inner housing 15 are employable to engage female threads on the battery removable backshell 16. Also included in the inner housing is a battery stop 124, which extends across the inner diameter of the housing so as to block movement of the batteries relative to the electronics within the housing. The inner housing 15 is sized such that its outer diameter is only slightly smaller than the interior diameter of the outer housing 13. In order to connect the sensor head 30 to both the inner and outer housing, the inner housing will first rotatably engage the threaded portion of the sensor head. The outer housing may then be slid over the inner housing and then the outer portion of the sensor head, so as to compress and engage the seals dispose thereon.

One advantage of the two-piece housing 12 described above is that any number of different materials may be employed for both the inner and outer housings. Further, the inner and outer housings are configured such that they are both easily replaceable. For example, in the situation where a user wishes to switch outer housing materials (such as from stainless steel to plastic), all that is required is the removal of the battery removal backshell, sliding the outer housing over the engaging seals of the sensor head, removing the outer housing, sliding on a new outer housing, and then replacing the battery removal backshell.

Figure 12A:
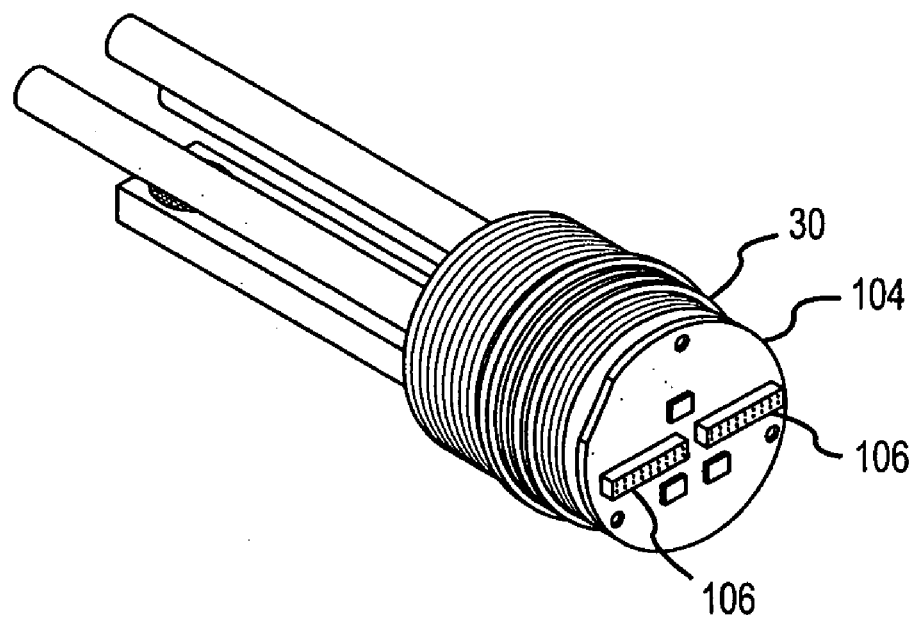
FIG. 12 shows an assembled view of the analog circuit card with sensor head.
FIG. 12b discloses an explode perspective view barometric and FIG. 12c discloses a perspective view of the analog circuit card.

As was mentioned above, the circuit board 104 and main circuit board 100 are connectable in a manner which, for the most part, avoids the use of external wires and wire harnesses which require the use of soldered electrical connections to circuit boards. Disclosed in FIG. 12a is a geometric view of the sensor head 30 with circuit board 104 attached thereto. Shown in particular are female connectors 106 mounted on the exposed side of the circuit board. Connectors 106 comprise a number plugs, each configured to receive a conductive pin of a matching electrical connector mounted in the sensor head.

Figure 12B:
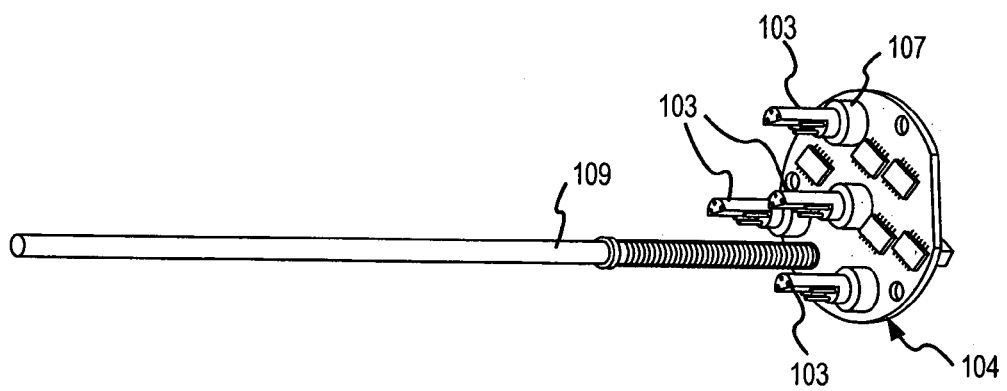

Disclosed in FIG. 12b is a view of circuit card 104 showing in particular the connectors which pass within the sensor head 30. The electrical connectors 103 are wired via the circuit card 104 to female connector 106. Also mountable on the circuit card 104 is a temperature probe which extends therefrom. In the perspective view shown in FIG. 12b, it is seen that each of the connector plugs 103 includes a number of female and male electrodes configured to electrically connect with matching electrical connectors which are included in the sensor head components described above. Disposed around the exterior surface of each of the plugs 103 is a radially compressive sealing device 107 which provides an environmental seal in the sensor ports when these components are engaged. Also extending from the circuit board 104 is a temperature probe 109 which also is configured to pass within the sensor head 30. Included thereon is another compressible sealing device mounted proximate to a spring.

Figure 12C:
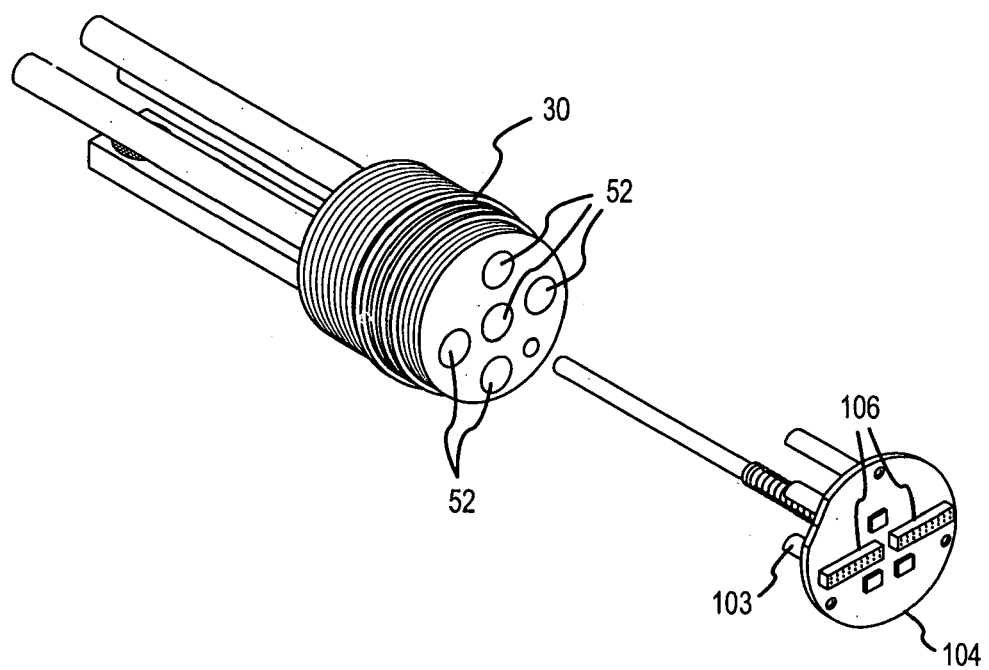

Disclosed in FIG. 12c is a perspective exploded view of the sensor head 30 and circuit card 104 which shows in particular the manner in which the connectors pass within the sensor head 30. Shown on the sensor head 30 are ports 52 which are configured to receive the various connectors 103. When assembling the sensor head and circuit card 104, each of the connectors 103 is aligned with a particular port 52 and the connector passes within the port 52. The radially compressive sealing device 107 which encircle each of the connectors then provides an environmental seal. Fasteners may then be employed to fixably attach the circuit card 104 to the sensor head 30.

Figure 13:
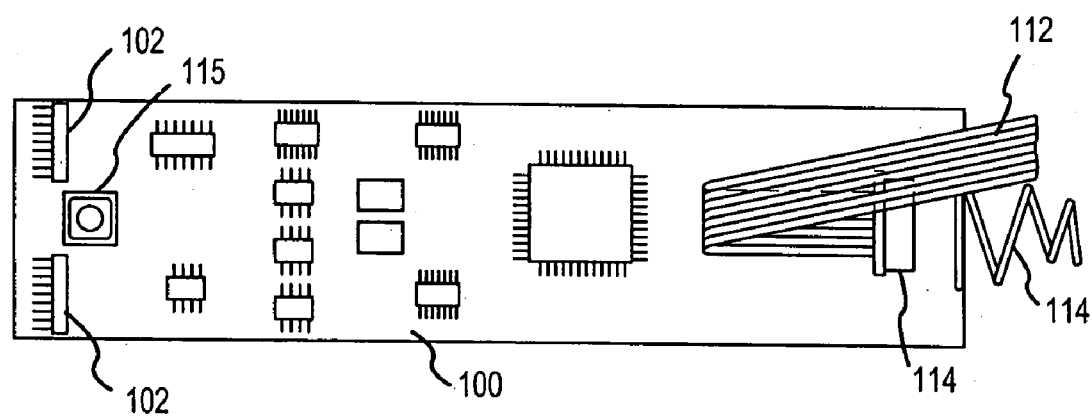
FIG. 13 shows a side view of the main circuit board including barometric pressure sensor.

As was described above, the circuit board 104 is connectable to a main circuit card 100. Disclosed in FIG. 13 is a side view of main circuit card 100. Included on the circuit card 100 are male connectors 102 each configured to electrically engage with the female connectors on circuit board 106. In order to establish an electrical connection between circuit board 104 and main circuit board 100, the pins extending from electrical connectors 102 are aligned with the appropriate plugs in connectors 106. Once the plug-in connection is established, the main circuit board will cantilever perpendicular from the circuit board 104 as well as sensor head 30 in a manner which is enclosable within housing 12. The inner diameter of the inner housing 15 is sized such that when the main circuit board 100 is extending from circuit board 104, the interior surface of housing of provides support to the circuit board.

Also included on the main circuit card 100 is barometric pressure sensor 115. The mounting of this barometric pressure sensor within the housing 12 provides for taking atmospheric pressure readings within this enclosure and then electrically providing this reading to the electronics for the tool assembly. As will be described in greater detail below, the data quick connect device with associated data line includes a fluid path way which provides atmospheric pressure within the housing 12. Anyone skilled in the art would realize that the barometric pressure sensor 115 may be mounted anywhere within the enclosure so as to provide a local pressure reading.

Also attachable to main circuit card assembly 100 is electrical connector 114 and data ribbon 112. This combination of components provide for the receipt and transmission of electrical signals to the far end of the tool assembly. Further, a spring 144 may be connectable to the circuit card so as to provide a grounding contact for the batteries positionable within the tool assembly.

Figure 14A:
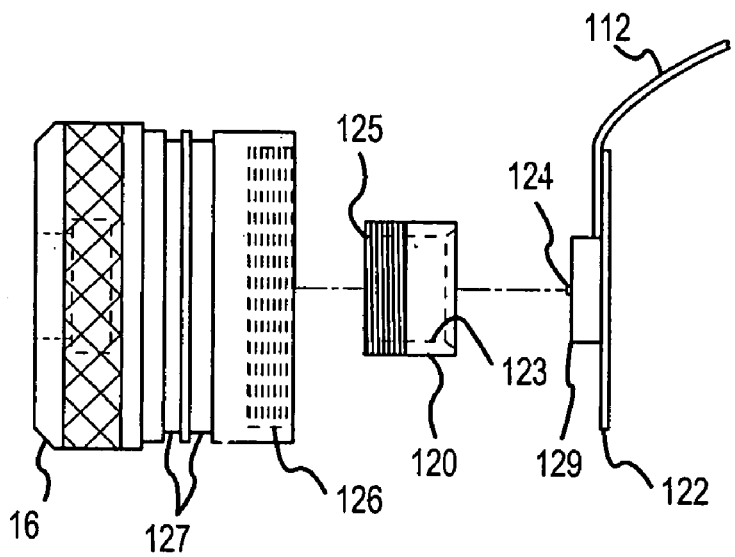
FIG. 14a-c discloses views of the removable backshell including electrode.

The tool assembly 10 described herein further includes features for providing an uninterruptible power connection to the electronics in a manner which allows for the removal and reattachment of the data quick connect cable 20. Disclosed in FIG. 14a is an exploded view of the removable backshell 16. Included in the backshell are female threads 126 which are configured to engage the male threads on the inner housing 15 when the tool assembly is assembled. Grooves 127 are configured to receive radially compressive sealing devices so as to engage the outer housing 13 upon assembly of the tool. As with the engagement between the sensor head and the outer housing, engagement occurs by sliding the outer housing over this portion of the backshell until the stop portion is contacted. Also included as part of the battery removable backshell is insert 120, which compressively fits within the cover and provides for the positioning of electrode assembly 122. Passage 123 through the insert 120 is configured to include a set of female threads 125 which are sized to engage with data quick-connect device 18. In connection with electrode assembly 122 is the data ribbon 112, which runs to the main circuit board along the length of the interior of the tool assembly.

Figure 14B:
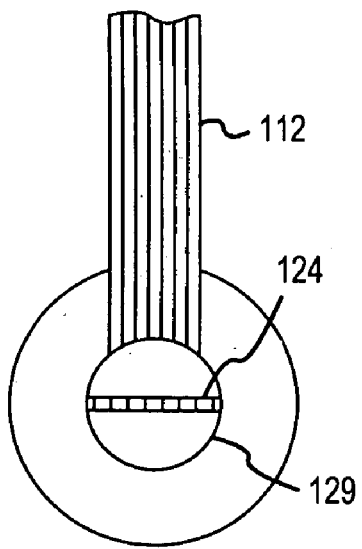
Figure 14C:
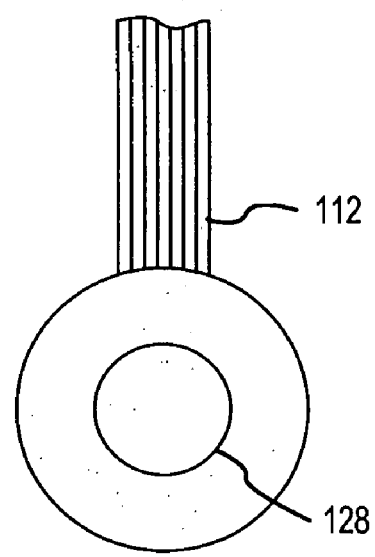

Passage 123 is also sized to receive insulative layer 129, within which multiple connector unit 124 is configured. A front view of connector unit 124 is shown in FIG. 14b. The multiple connector unit 124 is comprised of an elastomeric material upon which conductive traces are disposed. The multiple connector unit is described in detail in U.S. Pat. No. 6,305,944 which is hereby incorporated, in its entirety, by reference. The opposite side of electrode assembly 122 is show in FIG. 14c. Included therein is electrode 128 for providing an electrical contact to the batteries. Power from the batteries is also delivered to the tool assembly electronics through connector ribbon 112.

Figure 15A:
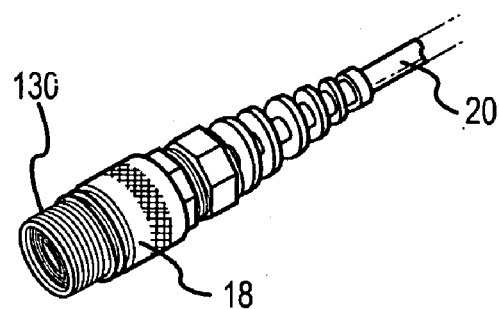
FIG. 15a-b discloses views of the data quick connect including printed circuit board.

The final mechanical portion of the multi-parameter monitoring tool assembly 10 is the quick-connect device 18 and associated data line 20. Disclosed in FIG. 15a is a geometric view of the quick-connect device. Included therein is a threaded portion 130 which is specially configured to engage the threaded portion 125 in the removable backshell. Extending therefrom is data line 20 which can be of any known construction and include enough conductive lines which provide for the transmission and receipt of necessary data (and power) signals. The data line 20 is further configured to include a fluid pathway which provides atmospheric pressure to the interior of the housing when the quick connect device is connected to the backshell. The quick-connect device is removable from the assembly through disengagement of the threaded portion 130 from the removable backshell. As can be seen from reviewing the structure of the removable backshell, the backshell itself would remain engaged thus continuing to apply the necessary pressure through electrode 128 so as to maintain a power connection for the monitoring tool assembly electronics over data ribbon 112.

Figure 15B:
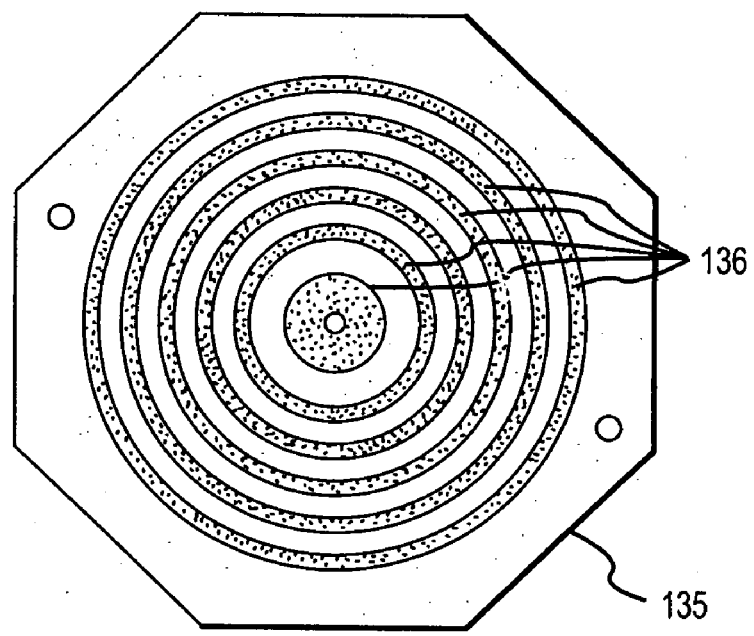

In order to provide for the proper alignment of the different conductive lines within data line 20, the quick-connect device includes a printed circuit board 135 substantially as shown in FIG. 15b. This printed circuit board is specially configured for establishing individual electrical connections through conductors 136 with the multiple connector unit 124 through application of a compressive force generated through engagement of the threaded portions. The manner in which this connection is established is described in U.S. Pat. No. 6,305,944 which, as was mentioned above, is incorporated in its entirety by reference.

Figure 16:
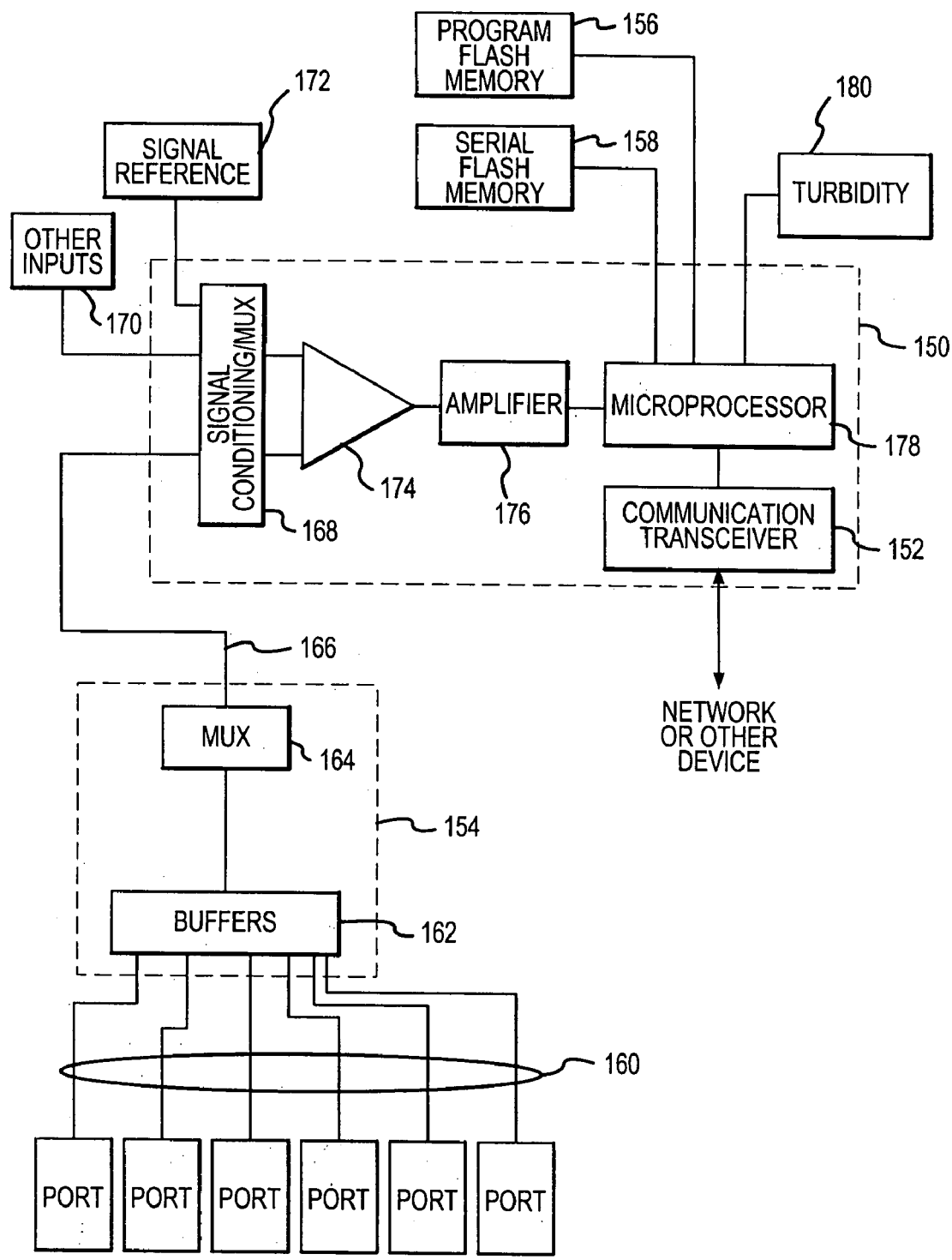
FIG. 16 discloses a system diagram for the electronics portion of the tool assembly.

With regards to the electrical system portion of the tool assembly, disclosed in FIG. 16 is an electrical system diagram for the multi-parameter tool assembly which, as will be described in greater detail below, is connectable to any number of different types of communications networks. The electronic system may be broken down into two major components: the analog card 154 and the main card 150. Included on the main card 150 is a microprocessor 178, which provides for the internal routing of electrical signals and the execution of various programming included in the firmware stored in memory. In connection with the microprocessor 150 is a communications transceiver 152. The transceiver performs a conversion between communication formats for signals transmitted from the tool assembly over the communications network. The transceiver also provides for format conversion of signals received over the communications network.

Also in connection with the microprocessor 178 are the program flash memory 156 and the serial flash memory 158. Program flash memory 156 is employed to store the version of firmware which the tool assembly employs for its operation. Incorporated in the firmware are a number of processes which the tool assembly employs in various aspects of its operation. The serial flash memory 156 is employed to download firmware upgrades as well as store data accumulated in tests performed by the tool assembly. Included in the main circuit board is signal conditioning/multiplexer 168. This components acts as the interface for receiving signals from one or more remote sources. These remote sources include the analog circuit board 154 as well as other sensor inputs 170, such as from a turbidity sensor. Another input may be signal reference 172.

Connecting the analog circuit board to the main circuit board is connector 166. As was described above, this connector 66 may comprise a male and female multi-pin connectors mounted on the circuit cards. Included within the analog board 154 may be multiplexer 164 employable for selectively activating each sensor head component as well as signal buffers 162. The signal buffers are connectable to each of the sensor ports via connectors 160.

One electrical connection establishable between the analog circuit board and each sensor head component interconnected with sensor head is a circuit which is activated, in that it is employed for monitoring a particular condition wherein a signal is naturally generated between electrodes in the circuit, and the magnitude of the signal is measured to identify one or more conditions. An issue which exist with regards to the employment of unactivated circuits in the tool assembly, is that because of the common circuitry employed for the different types of sensors, certain stray current may be created in these unactivated circuit which affect the accuracy of one or more of the measurements. One solution to substantially eliminating these stray currents is the use of the high impedance buffers 162 which are positionable in each of the circuits.

Figure 17B:
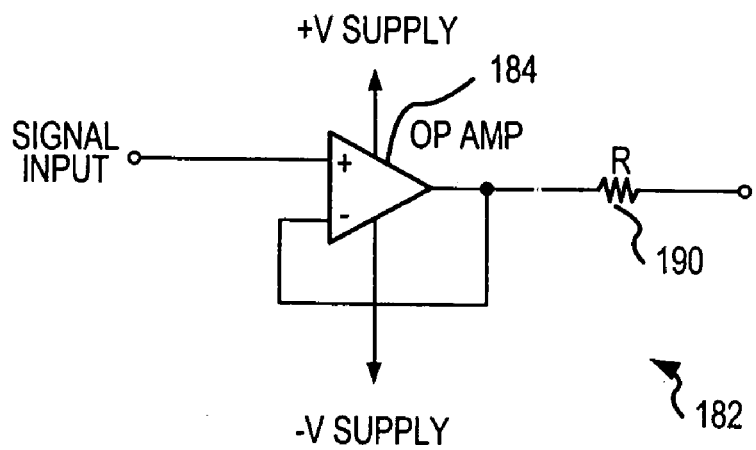
FIG. 17a-b discloses various configurations of the high impedance buffers employable in the tool assembly.
Figure 17A:
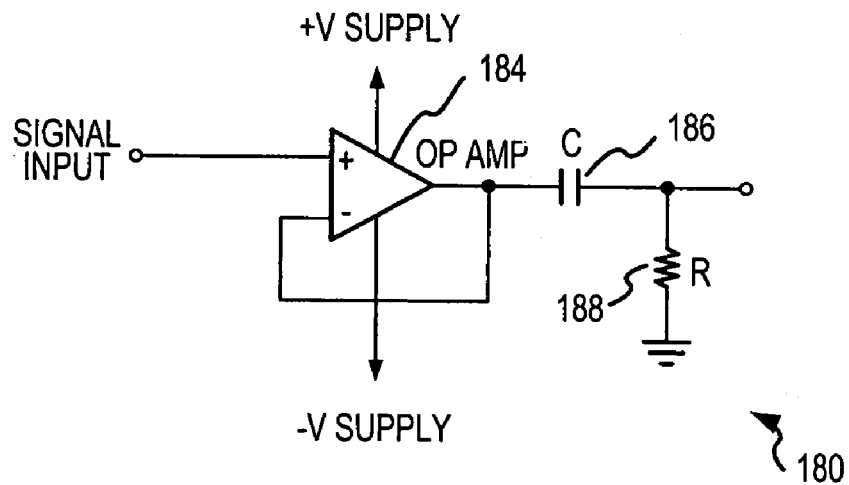

Disclosed in FIGS. 17*a* and *b* are two separate configurations of the buffer, one which is employable with ports which interconnect with both active and passive sensors and the other which employable with ports that only connect with passive sensors. Disclosed in FIG. 17*a* is an active sensor buffer 180 which includes an op amp 184. The op amp is always powered to provide an always active high impedance input. The op amp is further micro powered so as to maximize battery life. Capacitor 186 is included in the buffer to prevent current drive into unpowered circuitry. The resistor 188 provides DC bias for downstream circuitry. The values of resistance and capacitance for these elements may be chosen such that there is minimal attenuation of the signal being measured.

Disclosed in FIG. 17*b* is the configuration for the passive sensor buffer 182. As with the active sensor buffer, an always powered OP amp 184 is employed, which provides the active high impedance input. The resistor 190 at the output of the op amp is of the large ohm variety and minimizes the current drive into the unpowered circuitry. This high impedance input virtually eliminates leakage current through the sensor, which may affect sensor performance.

According to the various embodiments of the invention described herein, the connectors 160 may comprise anything from two wire connections to a multiple wire ribbon cable. As was discussed above, in a typical configuration, each of the typical sensor ports comprises electrodes to establish a six wire connection. Each connector employed with an interchangeable sensor also includes electrodes for establishing a six wire connection. In certain situations such as with a temperature, pressure, or turbidity sensor, more or less electrical connections are required. For example, a temperature sensor may be a simple two wire connection, and may be positionable on the sensor head 30 such that it does not employ any of the sensor ports for the interchangeable sensors. Returning again to FIG. 1*b*, it is seen that temperature sensor 33 which extends from sensor head 30 is positionable proximate to the interchangeable sensors but without employing a sensor port.

The sensor connections 160 may further comprise four wire or a six wire connectors configured for receiving and connecting with the interchangeable sensor head components. Most of the interchangeable sensor head components are configured to operate either over a four wire or six wire connection. More specifically, active sensors typically require a six wire connection (1 pair powering the sensor, 1 pair for the sensing element, and 1 pair to the EEPROM). Passive sensors typically only require 4 wire connection (1 pair for the non-activated sensing circuit, and 1 pair to the EEPROM). Accessories would typically require a powered pair to the motor portion and a pair to the EEPROM. The use of the EEPROM in systems operation will be described in greater detail below.

In one configuration of the invention, all of the ports may be configured with at least a four wire connection, however in certain situations, certain ports may be wired with six wires. If that is the case, the system described herein is further configured with detection software that detects when an active interchangeable sensor is used in a passive configured port. This detection process will be described in greater detail below.

In yet another configuration, the electronic connections 160 may established through use of a multi-wire ribbon which is connectable from the sensor to the analog circuit board through the port. In this situation a specially configured port may be employed. For example, a pressure sensor may require at least a ten wire connection in order to operate. In such a situation, the sensor plug may be specially configured such that the pressure sensor is not removable and a more permanent set of connections is established.

In operation, the program flash memory 156 has stored thereon programming for tests or operations which are to be performed by various components of the tool assembly. This includes individual tests for each parameter to be monitored. As a first step in the operation, a determination may be made as to what type of sensor head component is connected in each port. Once the current configuration of a sensor head is established, the micro processor 178, using the programming provided in memory, initiates and performs the particular function, whether it be a test procedure for a sensor or performance of a function by an accessory. As will be described in greater detailed below, testing information may be periodically provided back to a central location. Amendments to the tests and changes in schedule may be periodically received from the central location and these changes are implemented by the micro processor per the received instructions.

The first function performed in particular with regards to the insertion of interchangeable sensors in a sensor head components head 30 is a determination as to whether the plug into which the interchangeable sensor has been inserted is compatible with the particular type of sensor. For example, sensor head components which require an active connection would not be employable in a passive wired plug. The electronics of the tool assembly includes programming which extracts data stored in the EEPROM for each interchangeable sensor head component upon insertion in a port. This data includes identification information for the particular component. For sensors in particular, calibration information can also be retrieved from EEPROM, which is then employable by the system in processing signal measurements. The advantage of including the calibration coefficient in the memory for the sensor is that the sensor does not then need to be field calibrated. More specifically, the particular sensor is employable with many different tool assemblies without the need to ever calibrate the sensor for the tool. Other information which may be stored in the EEPROM for the sensor head components includes manufacture date, calibration date, operational range, serial number, hardware revision, actual sensor serial number, actual sensor model number, and production technician ID code may be stored thereon. All of this information is extractable from the EEPROM and may be stored in flash memory for the tool assembly.

Continuing on with the sensor identification process, the tool assembly is preprogrammed to determine that certain sensors such as conductivity and dissolved oxygen require a an active drive connection and measurement, while other sensors such as ISE sensors only require a passive measurement connection. After a particular sensor is installed in a port, the processor for the tool assembly will determine whether a signal is being received over all the designated circuits for that type of sensor. If all signals are not detected, a determination is made that the particular sensor has been improperly installed and an error message is generated which may be included in a reply message to be transmitted back to the central location.

Once the configuration is set, the tool assembly described herein may be programmed to perform tests and initiate functions in response to signals received from a remote location or according to a pre-program schedule. Depending on the type and frequency of measurements to be taken, test programs can be established which provide for any number of test schedule scenarios. These scenarios may include taking readings simultaneously and taking readings in a sequential fashion. The advantage of the latter method is that a sequential method of taking measurements provides for the maximum conservation of power. Even when using a sequential measurement schedule, the frequency of certain measurements may be increase or decrease depending on the desired number of measurements.

Figure 18:
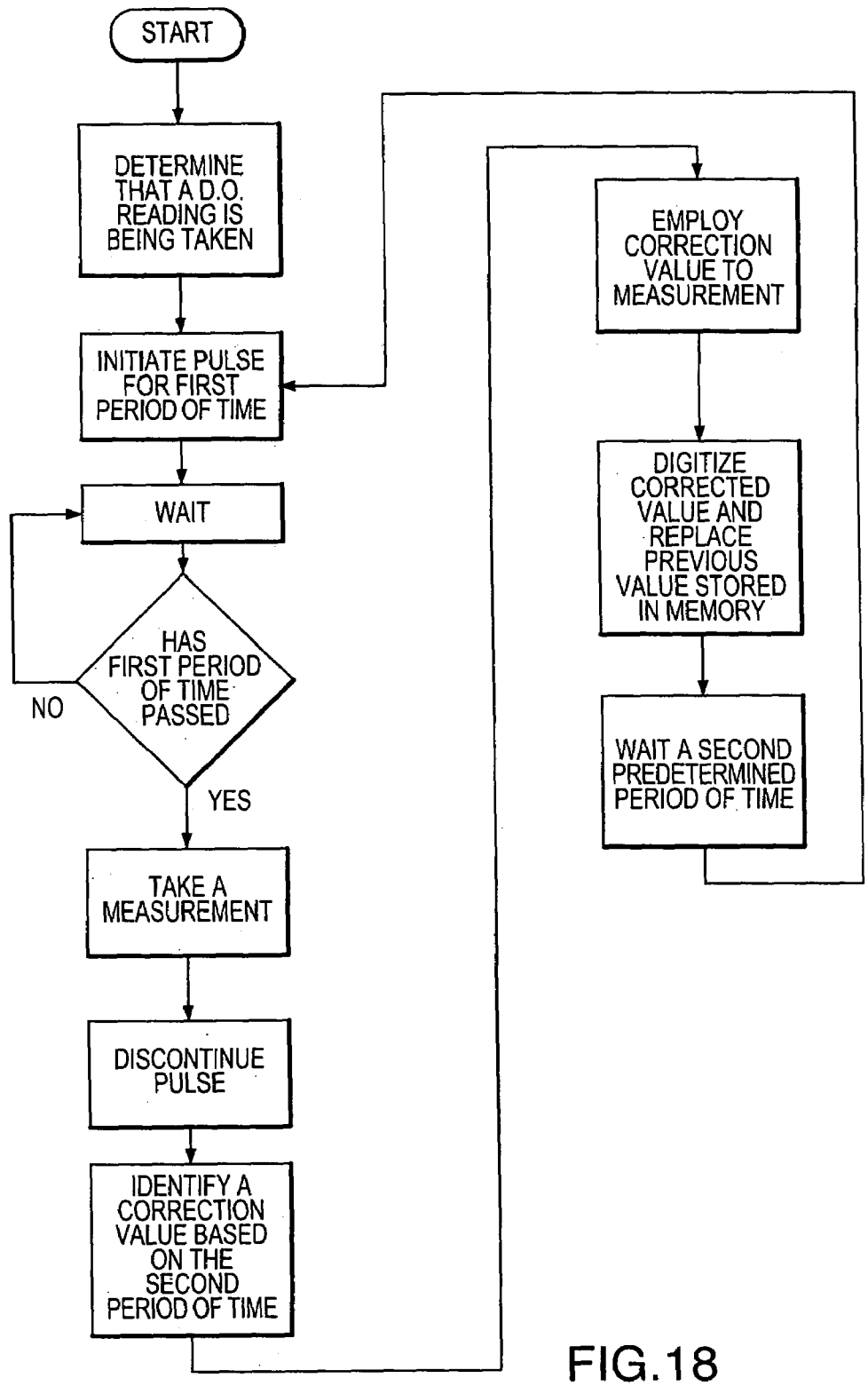
FIG. 18 discloses a flow chart which describes the steps performed in performing monitoring operations for the dissolved oxygen sensor.

In performing a monitoring process, typical steps include making an instantaneous measurement of signal strength across a particular circuit, and then using the calibration coefficients extracted from the EEPROM of the sensor in order to generate an accurate reading. This information may then be stored in memory and employed at a future time. Other measurements may require additional steps be performed in order to take a measurement. One of those measurements is the detection of dissolved oxygen. Provided in FIG. 18 is a flow chart which describes in detail the steps performed by the system described herein when taking dissolved oxygen readings. To begin, once the system detects that a dissolved oxygen sensor has been inserted in the sensor head, according to the programming provided for performing test, a dissolved oxygen reading is made part of the test schedule. As part of the initial communication with the dissolved oxygen sensor where identification and calibration information are extracted from the sensor EEPROM, a correction value may be included as part of this information.

To begin the monitoring process for dissolved oxygen, initially a pulse is transmitted over the powered circuit for the sensor over a first predetermined period of time. After waiting a second predetermined period of time, a reading is taken across the activated circuit in the sensor. Once the reading is taken, the circuit is deactivated and the correction value is retrieved from memory and then used to correct the measured value so as to provide an accurate dissolved oxygen reading. This correction value may be directly related to time periods employed in the test schedule, such as the time between when a pulse is initiated and when the measurement is taken, as well as the total time between the end of the last pulse and the initiation of a new pulse. As is well known, a typical dissolved oxygen sensors require that a certain amount of time pass between the initiation of the pulse and a measurement so that the volume in which the measurement is taken stabilizes. In order to save energy and time, the system described herein employs the correction value to account for the manner in which the dissolved oxygen reading stabilizes over time.

Once the dissolved oxygen reading is taken, the corrected value that may then be digitized and stored in memory for future access. The system may be set up such that each subsequent reading overwrites the previous reading in memory. The system may be configured such that upon request of a dissolved oxygen value, the last stored value is provided.

As was discussed above, the communications transceiver 152 is employable with a multi-parameter sensor assembly described herein in order to communicate with one or more remotely located devices. As such, the tool assembly is employable in various communications networks. Disclosed in FIGS. 19a–d are system diagrams for various configurations of communications networks within which one or more of the tool assemblies may communicate with a remotely located central controller. According to the invention described herein, a central controller may comprise a computer workstation which has software installed thereon specially configured for communicating with the multi-parameter tool assemblies described herein. The workstation also includes a connection to a communications network as well as means for communicating over same.

The central controller may also comprise various devices such as a palm top computer locatable near one or more the tool assemblies but able to communicate to a number of the tool assemblies over the communications network. The central controller may also comprise a specially configured well top device configured to communicate with the tool assemblies located at the particular well where the well top device is located, as well as other tool assemblies interconnected through the communications network. In yet another configuration of the invention, one or more of the tool assemblies may be configured to directly communicate with one or more other tool assemblies in the communications network. A system user may also alter operations of a particular accessory connected to a tool assembly. Through the same dialog boxes employed for viewing and amending parameters, the current configuration of the attached accessories may be presented and a schedule for performing various functions. Through the dialog boxes presented on the screen display, the schedule changes may be implemented for a particular accessories and then this information transmitted over the communications network to the identified tool assembly. This information is then stored in memory within the particular tool assembly.

Figure 19A:
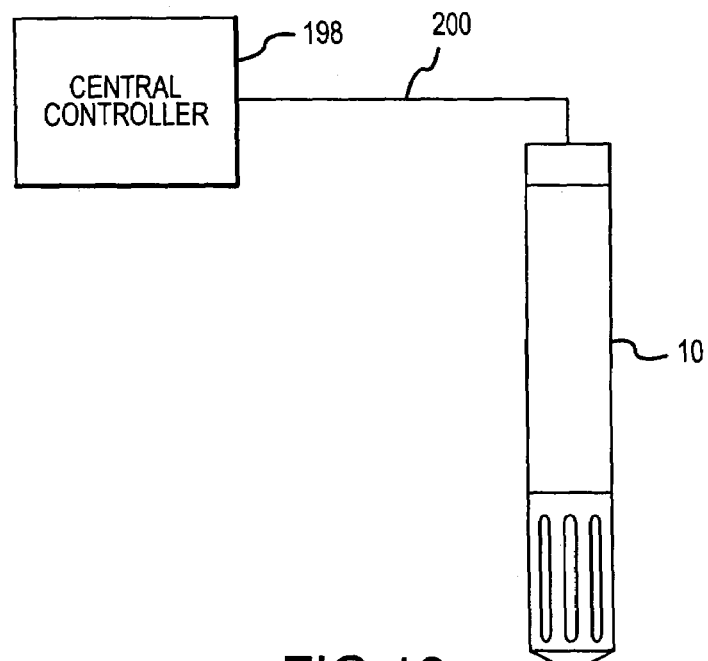
FIG. 19a-d is a system diagram which show the various configurations of the communications network employable to connect with the multi-parameter monitoring tool.

In the simplest configuration shown in FIG. 19a, the use of a communications network may not be required. A direct connection is established between the communications transceiver in the monitoring tool with the central controller. The connection in this situation may simply be a data line with sufficient bandwidth in order to handle these types of communications. In situations where the line is employed to provide power to the tool, a power line running from a power source may be incorporated therein.

Figure 19B:
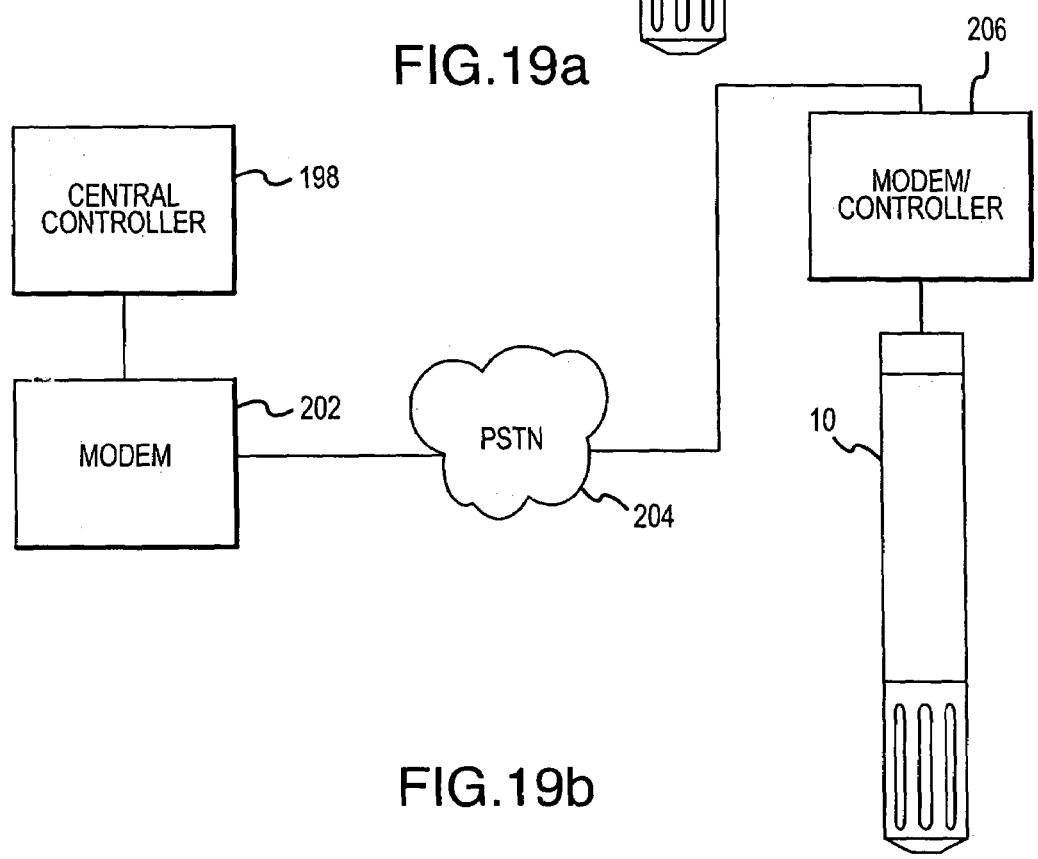

Disclosed in FIG. 19b is a configuration of a communications network in which the public switch telephone network (PSTN) 204 is employed as the medium for communications. In order to employ the PSTN, the central controller 198 is equipped with, or is in connection with, a modem 202. The modem is employed to establish a telephonic connection from the central controller over the PSTN 204. At a remote location, the modem/controller 206 is employed to establish a connection with the PSTN 204. The modem/controller 206 is in communication with the tool assembly 10. Functionality is also included in the modem/controller 206 to establish telephonic connections over the PSTN 204. The communications line may comprise a hard telephone line, or the modem/controller may comprise a cellular telephone device, which is employable to establish a telephonic connection over the PSTN via a wireless connection.

The modem/controller 206 may also comprise any number of devices such as a palm top computer such as a pocket PC or a palm pilot which includes a modem, a well top device or another tool assembly. Any of the controllers described above may be further configured to provide emulation of functionality for allowing one or more tool assemblies which employ a certain set of standards to communicate with a network which employs a different set of standards. Programming included in the controllers would allow the device to make the necessary conversions so that the different devices can communicate.

Figure 19C:
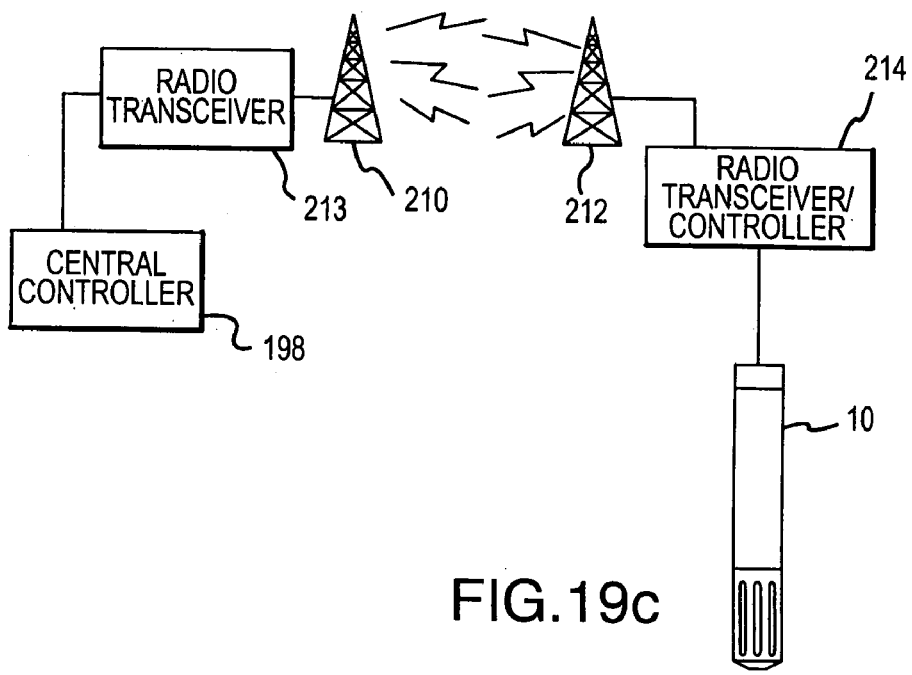

Disclosed in FIG. 19c is yet another configuration of the communications network wherein radio transceivers are employed to provide for the exchange of signals between the central controller 198 and any remotely located tool assemblies. In this configuration, a radio transceiver 213 is in electrical connection with central controller 198 and is configured such that data signals received from the central controller are converted to electromagnetic signals, which are transmitted via antenna 210. At the remotely located site, antenna 212 is in turn connected to radio transceiver/controller 214. A connection is then established from the transceiver/controller 214 to assembly 10.

Figure 19D:
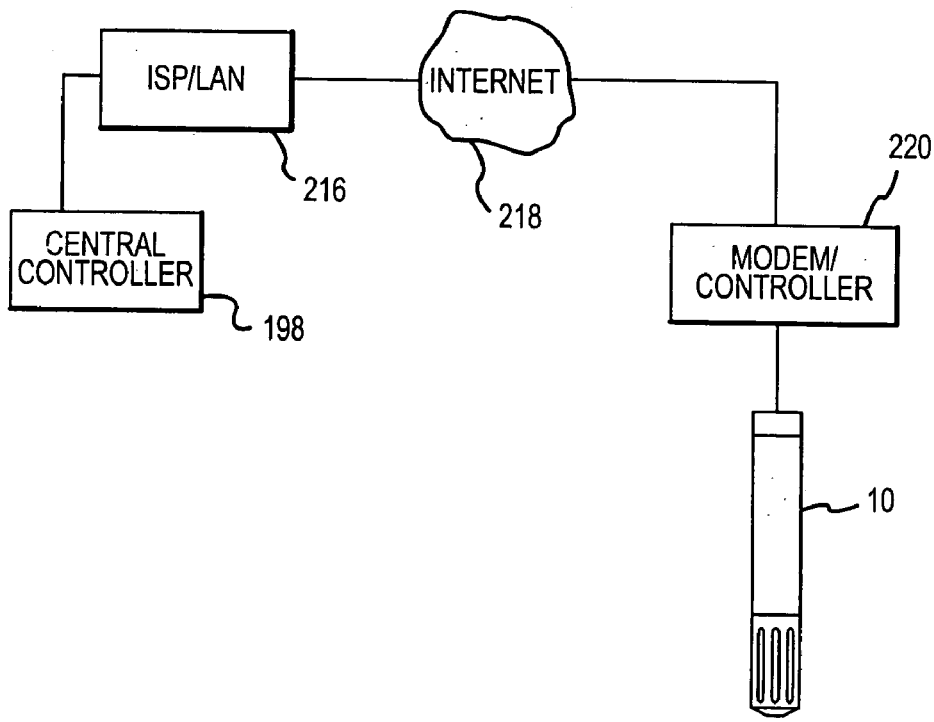

Disclosed in FIG. 19d is yet another configuration for the communications network. In this configuration, a communications network such as the Internet or a local area network (LAN) 218 may be employed as the medium to establish a line of communication. In one configuration of the invention, the central controller 198 may establish a telephonic connection with an Internet service provider 216 through which connections may be established over the Internet to the modem/controller 220 either through ISP 216 or directly to modem/controller 220 if it is employed as a node on the communications network. The modem controller 220 would also provide for the transmission of data signals back to central controller 198 over the Internet 218. One skilled in the art would realize that although only four configurations for a communications network are disclosed herein, any number of different configurations may be employable for establishing a line of communication between a central controller and one or more tool assemblies connecting to the communications network.

Figure 20:
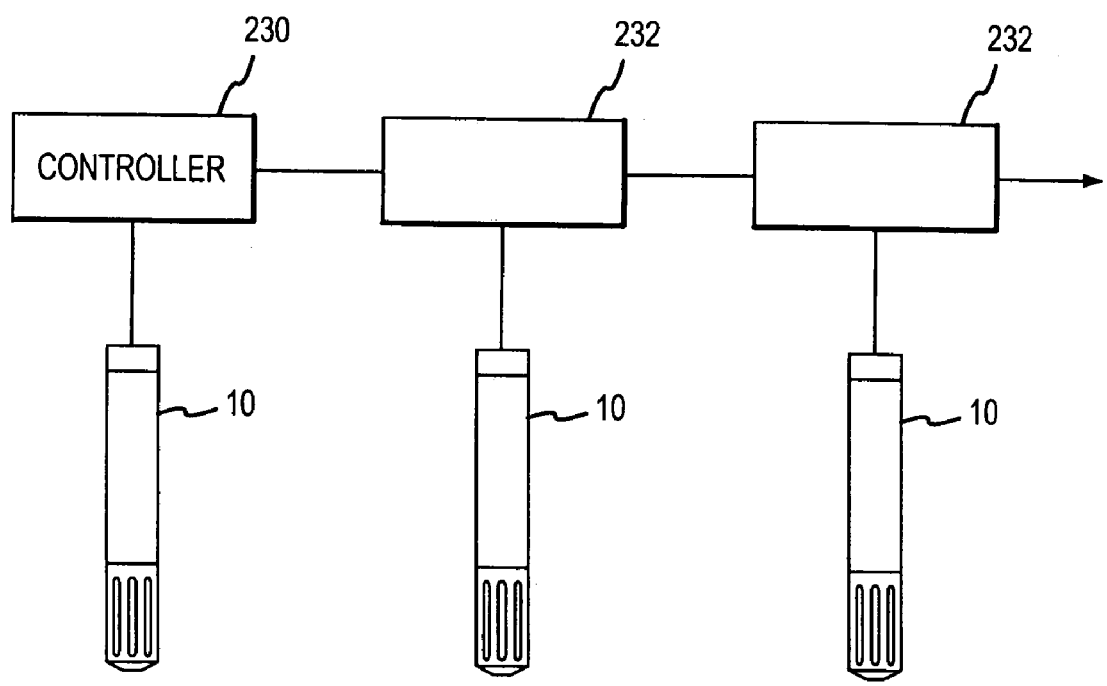
FIG. 20 discloses multiple multi-parameter monitoring tools connected in a network configuration.

As was mentioned above, a central controller may communicate with a plurality of multi-parameter tool assemblies over any of the communications networks. Disclosed in FIG. 20 is a system diagram showing a plurality of tool assemblies connected in a networked fashion. In order to establish a connection between tool assemblies and a remotely located controller, a plurality of network junction boxes 232 may be employed. These network junction boxes are configured to carry data and power signals to and from the tool assemblies connected in the network. Modem controller 230 provides for establishing the communication with a remotely located controller over any of the communications networks described above.

Figure 21:
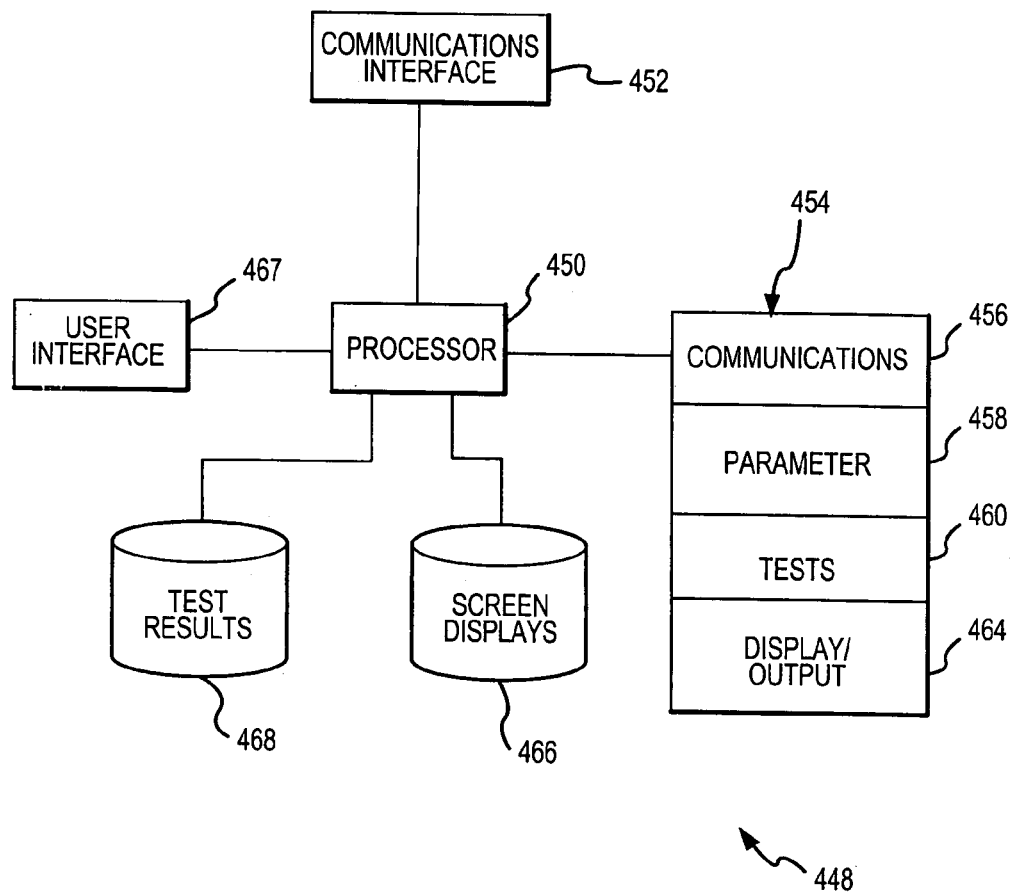
FIG. 21 discloses the system configuration for the central controller.

As part of the monitoring system described herein, the central controller 198 is specially configured to perform various functions with regards to communicating with the one or more tool assemblies connected in a network configuration. In one configuration of the invention, the central controller 198 may be a personal computer, palm top computer well top device, tool assembly, or other computing device upon which a monitoring system has been installed Disclosed in FIG. 21 is a system diagram, which shows in particular the monitoring system configuration for the central controller 198. Included in the central controller 198 is processor 450, which provides for internal routing of signals and execution of various processing modules. In electrical connection with the processor is communications interface 452 which provides for the processing of signals, which are received and transmitted from the central controller. The interface includes the necessary protocols for communicating over the different communications networks described above.

Also in connection with processor 450 is random access memory (RAM) 454, within which a number of the processing modules are loaded for performing the various functions of the monitoring system. The various processing modules may be initiated either automatically or through the receipt of various user inputs received from user interface 467. In one configuration of the invention, the user interface 467 may comprise a computer monitor, keyboard and mouse, or a pocket PC touch screen.

Returning again to the processing modules in RAM 454, included therein is communications module 456 which is employed to identify tool assemblies connected to the network as well the generation and transmission of messages and data over the communications network, a parameters modules 458 which is employed to display or change various parameter settings the tool assemblies and sensors employed when performing tests, tests module 460 which is employed to load automated tests schedules on to the tool assemblies, manually initiate test programs and to extract test data generated by the sensors from selected tool assemblies, and finally a display/output module 464 which is employed to display various screen displays through the user interface such that various user commands may be received and processed.

Also included in the central controller 198 are a number of databases which are employed to store information either generated by components in the communications network or used in operations of the monitoring system. Specifically, database 466 is used to store screen displays which are presented on the user interface such that system users may view system data and/or initiate various system functions. In one configuration of the invention, the monitoring system described herein maybe configured such that it operates in a Windows type environment and includes a number of pull-down menus and directory tree type structure for organizing information. For example, the communications network information may be organized in a screen display such that each COM port for the computer may be presented with its own node in a tree type directory structure. Beneath each of the COM port nodes may be a listing of the tool assemblies which communicate with the monitoring system through that particular node. Further, below each tool assembly node in the directory tree structure may be additional nodes which include itemized information for the sensor head components interconnected to the sensor head including parameters to be monitored or functions to be performed.

Associated with each node in the directory structure may be a screen display which presents information about the particular selection that has been made. With use of these display tools, the system user may move between screen displays to view information or initiate various functions which will be described in greater detail below. Also included in the central controller 198 is a tests results database 468. This database is employed to store and organize information which has been collected or extracted from the various tool assemblies.

As was described in great detail above, the tool assemblies described herein are configured to be positionable at locations remote from the central controller and to perform various tests and functions according to programming received from the central controller. As an example, the tool assemblies may comprise a surface monitoring multi-parameter monitoring tool assembly which is connectable to the communications network. The down well tool assemblies and/or surface monitoring tool assemblies include the functionality to take readings for the various parameters at designated times, store this data in a local memory and then provide this data when requested by the central controller.

Figure 22:
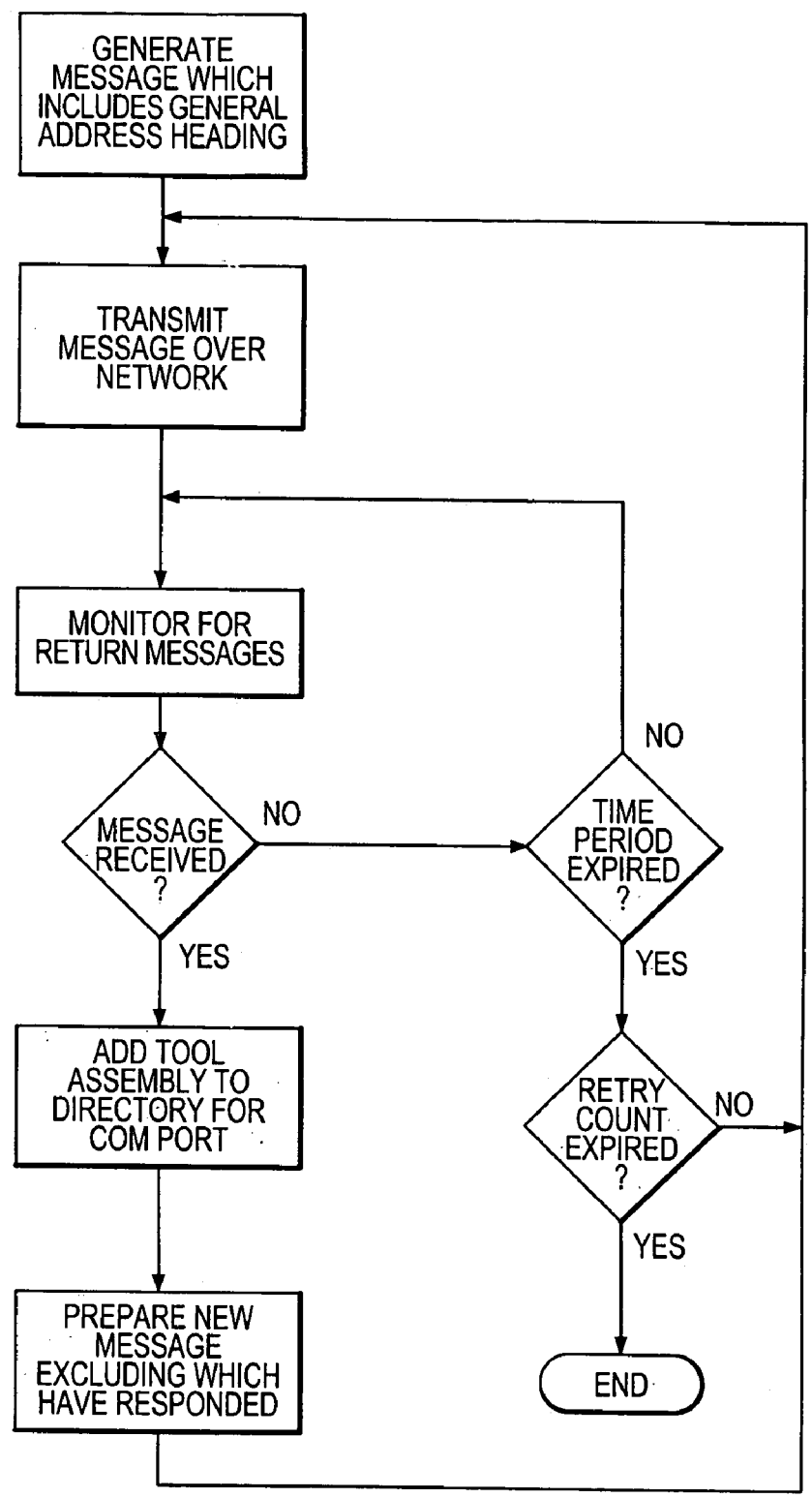
FIG. 22 discloses a flow chart which describes the steps performed by the central controller in identifying tool assembly connected to the communications network.

In operation, the monitoring system employed for communicating with the various tool assemblies is initially installed on the central controller. Once operational, a first step to be performed is to identify the tool assemblies, including sensor head components installed in the sensor head, which are connected to the network. Disclosed in FIG. 22 is a flow chart which describes the steps performed by the communications processing module in identifying which tool assemblies are connected to the communications network. As an initial step a selection may be by a system user as to which communications node will be analyzed. Once this selection is made, a general identification message is generated and transmitted over the communications network such that each tool assembly connected to that particular node will receive the message. In one configuration of the invention, communication between components is established through use of a message based system. The message to be transmitted is comprised of data packets wherein the message includes a address header which identifies the message destination. The communications network employed herein is "open" in that each of the components connected to the network receives all of the transmissions, but only processes those message that are either addressed specifically or are addressed generally.

Returning again to the flow chart of FIG. 22, each tool assembly which receives the message, will generate a reply message, which the central controller in turn will wait to receive. As each reply message is received at the central controller, the information provided by the replying tool assembly is logged in memory and may be presented on a screen display in the tree type directory structure. The reply information includes identification information for each tool assembly as well as the figuration information for the sensors currently interconnected in the sensor head. This configuration information includes the identification and collaboration information stored in the EEPROM in each of the installed sensor head components. A listing for the probe, including current sensor configuration, is also added to the directory for the corn port being employed.

If multiple tool assemblies are connected to the communications network, it is possible that two or more tool assemblies may transmit a reply message at the same time, thus creating the situation where only one or none of the reply messages is received by the central controller. As such, the central controller has been configured such that each of the tool assemblies may have multiple opportunities to reply if a particular message is not received by the central controller. Returning again to FIG. 22, when the central controller receives reply messages, it continually updates a list of tool assemblies connected to the communications network which have responded to the message. After the receipt and processing of each reply message, a new general message is generated and transmitted requesting that all tool assemblies on the network identify themselves. Additional instructions are included in the new general message which directs the tool assemblies which have already responded, not to respond further.

Upon transmission of the new general message, the central controller will wait a selected time period in order to receive a reply. If no reply is received after the time period has elapsed, the central controller will retransmit the message. The central controller will again wait a period of time in order to receive a reply message. If no reply message is received after set number retries of the general message the process will end and the tool identification process will be complete.

The above-described information is displayable for all tool assemblies which provide a reply message. In the situations where connections are being established from more than one central controller, information gathered during one connect session may be saved in a file and employed by other central controllers.

Once all of the tool assemblies on a particular COM port are identified, the monitoring system may be employed to transmit messages to one or more of these components. As was described above, each of the each of the tool assemblies runs on a energy conservation mode, or "sleep" when not communicating with the central controller or performing tests. One feature which has been incorporated into the system to further conserve energy is a selective activation process for selectively activating one or more tool assemblies when desired, without activating all the tool assemblies connected to a node. Messages which are generated by the central controller and transmitted to the individual tool assemblies are in the form of a data packets, which include an identifying byte in the header of the message. Included with the information stored about each of the tool assemblies stored in the central controller, is an multi-bit address header, which the central controller may employ when transmitting messages to particular tool assemblies. A general header may also be used in outgoing message to which all the tool assemblies will reply.

Figure 23:
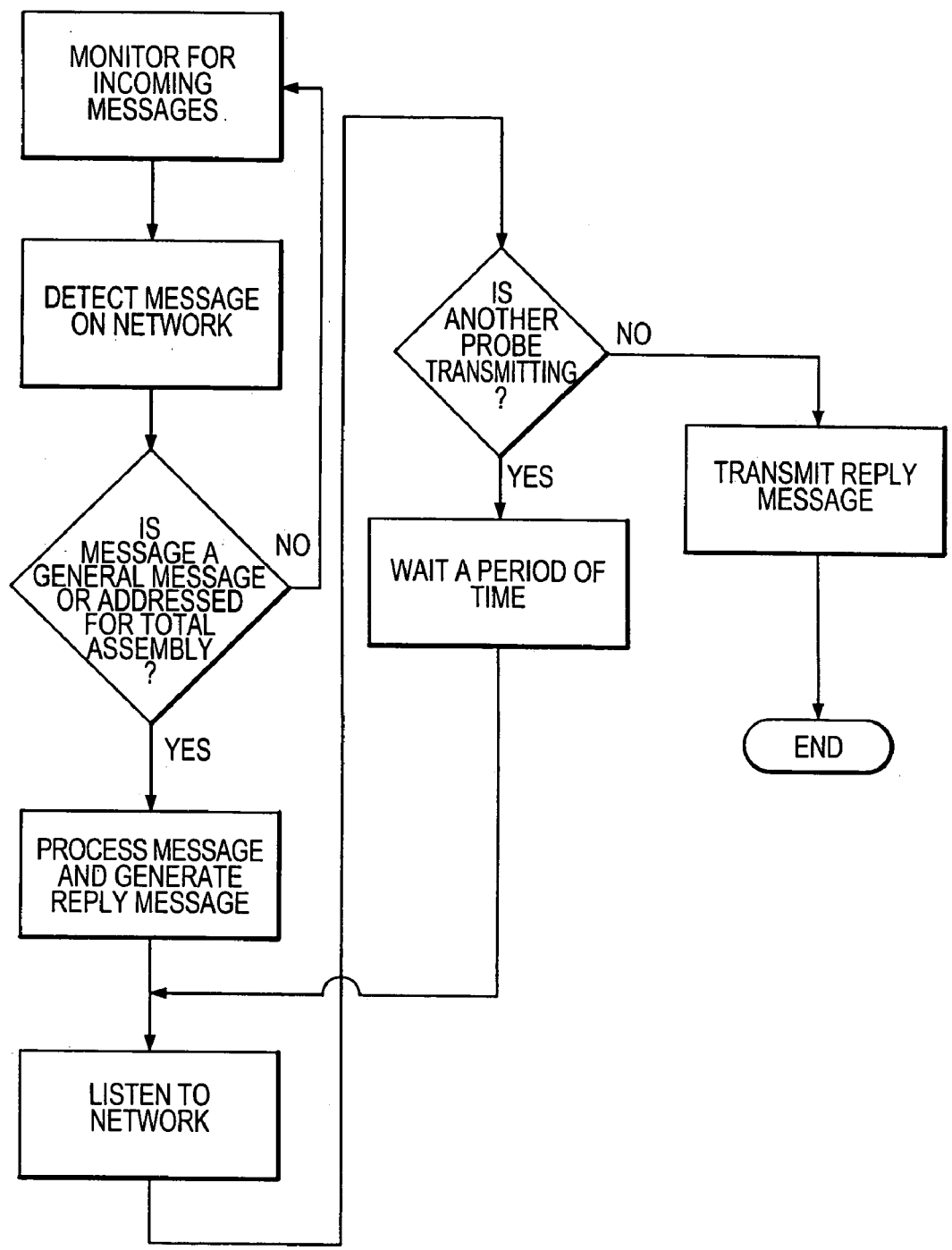
FIG. 23 discloses a flow chart which describes the steps performed by each of the tool assemblies connected to the communications network when transmitting messages to the central controller.

Disclosed in FIG. 23 is a flowchart which describes the steps performed by each of the tool assemblies which receive the messages. As was described above, each of the tool assemblies operates in a sleep mode wherein the tool assembly is turned off for the most part and is only operational to the extent that it monitors messages transmitted over the communications network. When the tool is in the "sleep" mode, it continually monitors the network for signals received and only activates when a message is detected which is addressed to the particular tool assembly or has a general message header.

Returning again to the flowchart in FIG. 23, during the sleep mode, a tool assembly will detect the receipt of an incoming message and perform the limited function of determining whether the message header includes the address for that particular tool assembly. Once the header is read, a query is made as to whether the message is a general message to which all tool assemblies connected to the communications network must respond. If this is so, the tool assembly is activated and the message is received and processed. If this is not a general wake-up message, the tool assembly makes a determination as to whether the message is addressed to that particular tool assembly. If the multi-bit message address matches the address for the particular tool assembly, it activates and begins processing the received message. If the multi-bit message address does not match the address for the particular tool assembly, the assembly stays in the sleep mode and continues monitoring incoming messages received over the communications network.

Also related to the selected activation of tool assemblies, is another feature incorporated into the system which provides a level of certainty that when messages are generated and transmitted over the communications network, replies are indeed received from all the tool assemblies which have been addressed. As was described above, one draw back of having an open communications network such as that described herein, is that when the central controller sends out a general message in which all the tool assemblies are to reply, the possibility exists that all of the tool assemblies will reply at the same time thus interfering with each other. According to the invention described herein, the tool assemblies are configured to provide some certainty that all reply messages from the tool assemblies are received by the central controller.

Returning again to the flowchart disclosed in FIG. 23, once an incoming message is determined to be a general message or addressed to that tool assembly, the tool assembly will activate, receive and process the message. After the processing is performed, the tool assembly will generate a reply message to be sent back to the central controller. At this point, the tool assembly will first monitor the communications network to determine if any of the other tool assemblies are currently replying. This monitoring step is performed so that two or more tool assemblies will not reply at the same time. If a determination is made that another tool assembly is currently replying, the replying tool assembly waits a period of time then check the network again to determine if any other tool assemblies are replying. If no other reply messages are detected, the tool assembly will transmit its reply to the central controller. The tool assembly will continue to try to transmit a reply message until a clear network is detected.

As was described above, the situation may occur where two tool assemblies do reply at precisely the same time to a general message and thus interfere with each other. As was described above, the central controller will periodically regenerate the message and transmit it so that the non-replying tool assemblies may respond. Once the messages are received, the steps disclosed in FIG. 23 are performed again by the tool assemblies.

The monitoring system described herein is employable by a system user to perform a number of different functions with regards to the one or more tool assemblies connected to the communications network. As was disclosed in FIG. 22, the central controller 198 includes a number of processing sub-modules which may be selectively employed to perform various monitoring functions. In particular, the parameters sub-module 458 is used to view and amend any parameters for any sensor in a particular tool assembly. The parameters for each sensor are stored in the flash memory for the tool assembly, and are provided to the central controller during the initial tool assembly identification process. A various points-in-time, the system user may initiate an extraction of data from a particular tool assembly so that the test results may be compiled and viewed. As with the other functions, a message for the particular tool assembly is generated and transmitted to said tool assembly and the tool assembly responds by compiling information with regard to the specified test and transmits such information back to the central controller for further processing.

When a system user wishes to view or amend a particular parameter of a sensor for a particular tool assembly, the listing of tool assemblies connected to a particular communications node may be displayed on the user interface and the tool assembly may be selected in order to view the sensors current installed and operating in the sensor head. In one configuration of the invention, a screen display is provided which displays all the parameter information with regards to a particular tool assembly. Through dialog boxes presented in the screen display, various parameter information may be entered or amended. If a system user wishes to add change parameters for sensors of a particular tool assembly, a message is generated by the central controller which includes the parameter information as well as an address heading for that particular tool assembly. This generated message is then transmitted over the communications network and once received by the tool assembly, and implemented into its programming.

Yet another processing module employed in the monitoring system described herein is directed to programming and implementing tests in the tool assemblies. Using the directory tree structure described above, the system user may select to view information about tests programmed for one or sensors in a particular tool assembly. Tests to be performed are stored on the flash memory for the tool assembly and a listing of the tests is provided to the central controller during the initial tool assembly identification process described above When this selection is made, a screen display may be presented which includes this program information. As was discussed previously, each of the tool assemblies include processing capability and memory. Stored into memory may be a number of automated tests which the tool assembly has been programmed to perform at designated intervals. When a system user selects to go into the testing mode for the system, the system user may retrieve and view information with regards to tests currently programmed into the device. This may be done for each sensor of each tool assembly. When viewing the information, the system user may have the option to manually initiate a program test or add a new test for one or more sensors. When adding a test, certain information and/or internal information may be entered, such as the particular sensor, and the type of test (linear, event, or linear average). Other options may be to program tests using adaptive scheduling. Steps performed in employing adaptive scheduling will be described in greater detail below.

Further, items which may be programmed for tests include measurement intervals for taking readings in an automated test as well as the point-in-time which a test is to begin. Once necessary information for the new test or the amended information is entered, the central controller may compile and transmit a message to the particular tool assembly instructing the assembly to load and execute the test.

As an additional feature of the system described herein, the system user may have the option of manually initiating or terminating a test for one or more sensors or a function of one or more of the accessories. The selection may be made through a dialog box in a screen display, and in turn, the central controller will generate a message for the particular tool assembly and transmit the same. According to the protocols described above, the central controller will then wait for a reply message either indicating that the test and/or function has begun or it has been stopped according to instructions.

As was discussed above, one mode of performing tests is called adaptive scheduling. Through use of adaptive scheduling, space in the flash memory for the tool assembly may be conserved by only storing data points measured after the occurrence of significant events. A test may be programmed to be performed when a particular condition is detected in any sensor, a customized monitoring program may be initiated and the data which is collected during this time period is specially identified. One example of a time when such a program may be employed is when a water table is monitored for such conditions as flooding or flash floods. When a significant event occurs which causes the water table rises, this condition is detected it may be advantageous to provide a continuous monitoring of the situation while it exists and then to discontinue the monitoring once the situation has passed. This also applies to measuring dramatic rises in the detection of contaminants.

Figure 24:
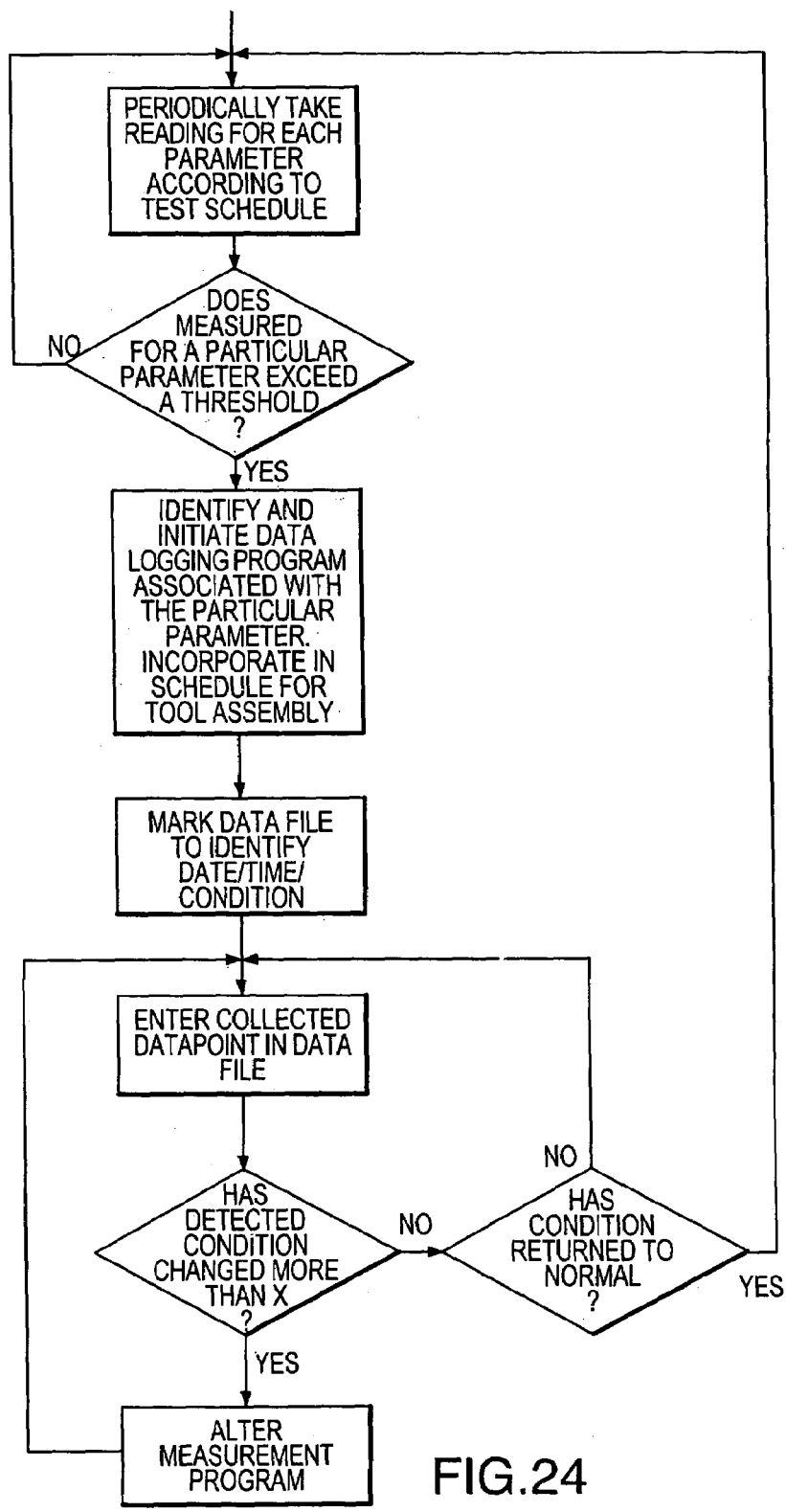
FIG. 24 discloses a flow chart which describes the steps performed by a tool assembly to collect data during the adaptive scheduling process.

Disclosed in FIG. 24 is a flowchart which describes in detail the step performed by a tool assembly during adaptive scheduling and monitoring. Initially the tool assembly may be operating in a mode where measurements are taken at set intervals but are not stored in memory. During the monitoring, a particular condition may occur which exceeds a threshold value for the monitoring condition. If this threshold value is exceeded, the tool assembly will access memory and retrieve a test program designated for monitoring conditions during the particular detected condition. As part of initiating the test program, an identifier is added to the first page of data collected by the tool assembly indicating such things as the date/time/condition of the initial event detected. From that point, data points may be periodically taken and stored in the data pages. In order to conserve memory, it is not necessary to associate dates and times with data points that follow as long as the readings are taken after known periods.

As the tool assembly and sensors continue monitoring, it may be detected that the measured condition has changed in a significant way which requires the use of another test program. For example, if the measured conductivity level exceeds a particular value, the frequency of readings taken may need to increase. When any type of change in test occurs, another identifier is added to the data page on which the new data points begins. As with the previous program, it may include date, time and condition which required the change. As was described above, additional readings may then be taken without the necessity of adding date or time information.

As the monitoring and the taking of data points continues, it may then be detected that the measured condition falls below the threshold of value and back to a "normal". At this point, the employment of the customized program may be discontinued and the sensors monitoring for that particular parameter returned to the idle mode wherein it only takes readings periodically and does not store them in memory. Adaptive scheduling may be performed for any number of different sensors in a tool assembly simultaneously. In the event that the test for the various sensors in a sensor head are performed sequentially, enough time would exist between the end of one sequence and the beginning of the next two performed any monitoring functions required by the adaptive scheduling procedure.

Yet another function performed by the test processing module of the central controller includes the extraction of test data for one or more sensors from the tool assemblies. When viewing particular tests for a tool assembly a selection may be made to extract data from the tool assembly for that particular test. Specifically, a system user may select the particular tool assembly in the directory tree structure and navigate to one or more existing tests for particular sensors. At this point, a selection may be made to extract test data for a particular sensor. In order to perform the above functions, the central controller will generate a message which is transmitted over the communications network and detected by the particular tool assembly. Once the message is received, the tool assembly will perform steps to extract the selected test data from the flash memory. This information is transmitted back to the central controller in a form of a message and through use of display/output module 464 disclosed in FIG. 21 and included in the central controller, the test information may be presented in the desired format. This may also be performed to retrieve a log of operations for an accessory.

Figure 25:
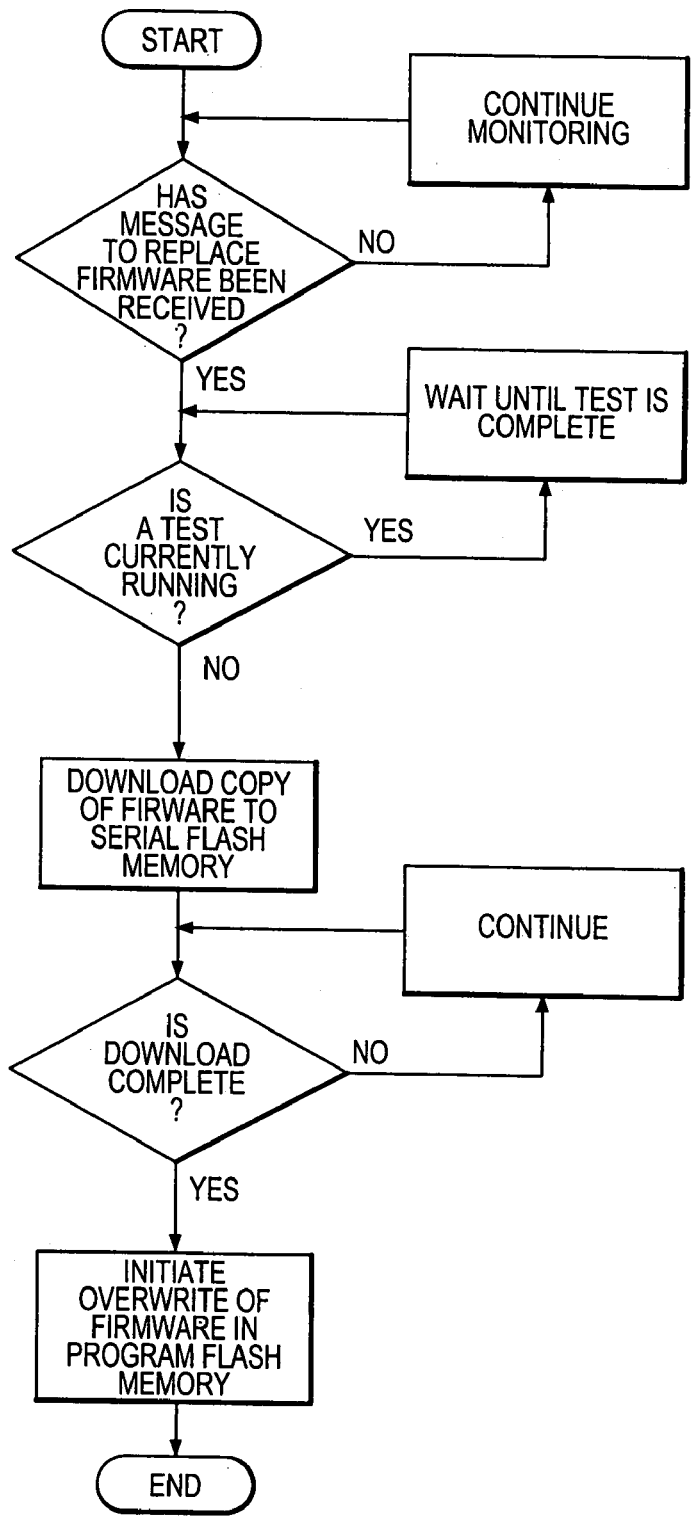
FIG. 25 discloses a flow chart which describes the steps performed in the upgrading or replacement of firmware in a tool assembly connected to the communications network.

One further feature of the system described herein is the functionality for a system user to update the firmware in a particular tool assembly as the firmware becomes available. Through the process described herein, it is done in a manner which ensures the integrity of the existing firmware as well as the new version which has been downloaded. To perform this process, a selection may be made to manually upgrade or replace the existing firmware. This selection may be made through use of an interactive screen display. If this selection is made, the central controller first identifies the appropriate firmware to be transferred and generates a message which includes the firmware. This message is then transmitted over the communication network to the particular tool. The steps performed by the tool assembly in downloading of the firmware is disclosed in FIG. 25.

Initially, the message is received from the central controller indicating that the firmware is to be downloaded. The tool assembly may at that point indicate that a test is being performed and the download cannot occur until the testing is complete. This is purely as an extra precaution to protect integrity of the firmware on the tool assembly. One skilled in the art would realize that the system may be configured such that the test can be performed and firmware downloaded at the same time. Once it is determined that a test is not currently running, an entire copy of the upgrade firmware is downloaded directly into serial flash memory 150, as shown in the system diagram of FIG. 16. The current version of the firmware is resident on the program flash memory 158. At any point after that the microprocessor may initiate a transfer of the upgrade firmware from the serial flash memory to the program flash memory. At this point the old firmware is overwritten. Once the transfer of the upgraded firmware is complete, a message is generated and transmitted back to the central controller indicating that the upgrade of the firmware was successful.

Various embodiments of the present invention have been described in detail. It should be understood that any feature of any embodiment can be combined in any combination with a feature of any other embodiment. Furthermore, adaptations and modifications to the described embodiments will be apparent to those skilled in the art. Such modifications and adaptations are expressly within the scope of the present invention, as set forth in the following claims.

What is claimed is:

1. A multi-parameter water quality monitoring system comprising:
   a plurality of multi-parameter monitoring tools each configured to receive and electrically interconnect with a plurality of interchangeable sensor head components and to communicate over a communications network; and
   a central controller connectable to the communications network, said central controller is configured to communicate with each of the multi-parameter monitoring tools, wherein the central controller includes functionality to receive configuration information for each of the plurality of interchangeable sensor head components interconnected with each of the plurality of tool assemblies and to extract operational information therefrom;

wherein each of the monitoring tool assemblies may be further configured to communicate directly with at least one other tool assembly over the communications network.

2. A multi-parameter water quality monitoring system comprising:
a plurality of multi-parameter monitoring tools each configured to receive and electrically interconnect with a plurality of interchangeable sensor head components and to communicate over a communications network; and
a central controller connectable to the communications network, said central controller is configured to communicate with each of the multi-parameter monitoring tools, wherein the central controller includes functionality to receive configuration information for each of the plurality of interchangeable sensor head components interconnected with each of the plurality of tool assemblies and to extract operational information therefrom;
wherein the plurality of tool assemblies are located at a site remote from the central controller and connection to the communications network is provided through use of a modem/controller device.

3. The system of claim 2 wherein the modem/controller employed for communicating over the network includes the functionality to emulate at least one other system such that communications may be established with devices other than the central controller.

4. A multi-parameter water quality monitoring system comprising:
a plurality of multi-parameter monitoring tools each configured to receive and electrically interconnect with a plurality of interchangeable sensor head components and to communicate over a communications network; and
a central controller connectable to the communications network, said central controller is configured to communicate with each of the multi-parameter monitoring tools, wherein the central controller includes functionality to receive configuration information for each of the plurality of interchangeable sensor head components interconnected with each of the plurality of tool assemblies and to extract operational information therefrom;
wherein the central controller comprises at least one of: a personal computer, a palm top computer, a well top device, and another tool assembly.

5. A multi-parameter water quality monitoring system comprising:
a plurality of multi-parameter monitoring tools each configured to receive and electrically interconnect with a plurality of interchangeable sensor head components and to communicate over a communications network; and
a central controller connectable to the communications network, said central controller is configured to communicate with each of the multi-parameter monitoring tools, wherein the central controller includes functionality to receive configuration information for each of the plurality of interchangeable sensor head components interconnected with each of the plurality of tool assemblies and to extract operational information therefrom, wherein the central controller is further configured to detect each of the tool assemblies connected to the communications network, selectively access each of the one tool assemblies, and communicate with each of the tool assemblies so as to access, amend, and retrieve information stored in the accessed tool assembly, including data relating to each of the interchangeable sensor head components interconnected with the accessed tool assembly;
wherein the operational information includes identification for each of the interchangeable sensor head components interconnected with a particular one of the plurality of multi-parameter tool assemblies;
wherein the interchangeable sensor head components comprise at least one of: an interchangeable sensor and an accessory; and
wherein the central controller is further configured to generate and amend a test schedule for each of the interchangeable sensors in the tool assembly, and to further access and extract data stored in memory for monitoring processes performed by each of the interchangeable sensors in the tool assembly.

6. A multi-parameter water quality monitoring system comprising:
a plurality of multi-parameter monitoring tools each configured to receive and electrically interconnect with a plurality of interchangeable sensor head components and to communicate over a communications network; and
a central controller connectable to the communications network, said central controller is configured to communicate with each of the multi-parameter monitoring tools, wherein the central controller includes functionality to receive configuration information for each of the plurality of interchangeable sensor head components interconnected with each of the plurality of tool assemblies and to extract operational information therefrom, wherein the central controller is further configured to detect each of the tool assemblies connected to the communications network, selectively access each of the one tool assemblies, and communicate with each of the tool assemblies so as to access, amend, and retrieve information stored in the accessed tool assembly, including data relating to each of the interchangeable sensor head components interconnected with the accessed tool assembly;
wherein the operational information includes identification for each of the interchangeable sensor head components interconnected with a particular one of the plurality of multi-parameter tool assemblies;
wherein the interchangeable sensor head components comprise at least one of: an interchangeable sensor and an accessory; and
wherein the central controller further comprises at least one user interface which is configured to display a plurality of screen displays which provide for the viewing and/or manual entry of information relating to the operations of the at least one tool assembly including the data for each of the interchangeable sensor head components connected thereto user commands.

7. The system of claim 6 wherein the central controller is configured to perform at least one of:
detecting whether the at least one tool assembly is connected to the network;
detecting which of the interchangeable sensor head components is interconnected with the at least one tool assembly;
presenting a first screen display which provides detail configuration for the at least one tool assembly connected to the communications network including the data for each of the interchangeable sensor head components connected thereto;

presenting a second screen display which provides for manual entry of parameter information for each of the interchangeable sensors interconnected with the at least one tool assembly, wherein the entered parameter information is provided to the at least one tool assembly over the communications network; and presenting a third screen display for manual entry of testing information for each of the interchangeable sensors interconnected with the at least one tool assembly, wherein the entered test information may be provided to the at least one tool assembly over the communications network; and extracting and compiling test information for each of the interconnected interchangeable sensors from the at least tool assembly.

8. A multi-parameter water quality monitoring system comprising:

a plurality of multi-parameter monitoring tools each configured to receive and interconnect with a plurality of interchangeable sensor head components and to communicate over a communications network; and a central controller connectable to the communications network, said central controller is configured to communicate with each of the multi-parameter monitoring tools, wherein the central controller includes functionality to receive configuration information for each of the plurality of interchangeable sensor head components interconnected with each of the plurality of tool assemblies and to extract operational information therefrom, wherein the central controller is further configured to detect each of the tool assemblies connected to the communications network, selectively access each of the one tool assemblies, and communicate with each of the tool assemblies so as to access, amend, and retrieve information stored in the accessed tool assembly, including data relating to each of the interchangeable sensor head components interconnected with the accessed tool assembly;

wherein the central controller is further configured to selectively address each of the tool assemblies by placement of a unique address header in a message generated for transmission over the communications network;

wherein the message may comprise firmware which the tool assembly may employ for upgrade and/or replacement purposes.

* * * * *